US010925917B2

(12) United States Patent
McFarland

(10) Patent No.: US 10,925,917 B2
(45) Date of Patent: Feb. 23, 2021

(54) POLYGONUM CUSPIDATUM EXTRACTS AS PHOTODYNAMIC INACTIVATING AGENTS

(71) Applicant: PhotoDynamic Inc., Halifax (CA)

(72) Inventor: Sherri McFarland, Colfax, NC (US)

(73) Assignee: PhotoDynamic Inc., Halifax (CA)

( * ) Notice: Subject to any disclaimer, the term of this patent is extended or adjusted under 35 U.S.C. 154(b) by 0 days.

(21) Appl. No.: 16/264,737

(22) Filed: Feb. 1, 2019

(65) Prior Publication Data

US 2019/0160129 A1 May 30, 2019

Related U.S. Application Data

(62) Division of application No. 15/282,118, filed on Sep. 30, 2016, now Pat. No. 10,350,255.

(60) Provisional application No. 62/236,114, filed on Oct. 1, 2015.

(51) Int. Cl.
| | | |
|---|---|---|
| A61K 36/704 | (2006.01) | |
| A01N 65/30 | (2009.01) | |
| A61N 5/06 | (2006.01) | |
| A61K 47/10 | (2017.01) | |
| A61K 9/00 | (2006.01) | |
| A61K 47/26 | (2006.01) | |
| A61K 9/06 | (2006.01) | |
| A01N 63/10 | (2020.01) | |
| A61K 41/00 | (2020.01) | |
| A61L 2/08 | (2006.01) | |
| A61L 2/10 | (2006.01) | |
| A61L 2/16 | (2006.01) | |

(52) U.S. Cl.
CPC ............ *A61K 36/704* (2013.01); *A01N 63/10* (2020.01); *A01N 65/30* (2013.01); *A61K 9/006* (2013.01); *A61K 9/0053* (2013.01); *A61K 9/06* (2013.01); *A61K 41/0057* (2013.01); *A61K 47/10* (2013.01); *A61K 47/26* (2013.01); *A61L 2/084* (2013.01); *A61L 2/10* (2013.01); *A61L 2/16* (2013.01); *A61N 5/062* (2013.01); *A61N 5/0624* (2013.01); *A61N 2005/0661* (2013.01); *A61N 2005/0662* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 7,977,516 B2 | 7/2011 | Souto | |
| 10,350,255 B2* | 7/2019 | McFarland | ............ A61K 47/10 |
| 2004/0052879 A1 | 3/2004 | Ravagnan | |
| 2010/0034757 A1 | 2/2010 | Fujii | |
| 2011/0281957 A1* | 11/2011 | Kuhrts | ............... A61K 9/06 |
| | | | 514/733 |
| 2012/0183633 A1* | 7/2012 | Kim | ............ A61K 36/704 |
| | | | 424/725 |
| 2013/0323335 A1 | 12/2013 | Rozenblat | |
| 2016/0120803 A1 | 5/2016 | Mathur | |
| 2018/0133118 A1 | 5/2018 | Deckner | |

FOREIGN PATENT DOCUMENTS

| | | | |
|---|---|---|---|
| CN | 1762431 | A | 4/2006 |
| CN | 102397345 | A | 4/2012 |
| CN | 103689007 | * | 4/2014 |
| CN | 104491157 | | 4/2015 |
| CN | 104825367 | | 8/2015 |
| JP | 2002029984 | | 1/2002 |
| JP | 2002212042 | | 7/2002 |
| JP | 2003551828 | | 10/2003 |
| JP | 2014506233 | | 3/2014 |
| WO | 2014138327 | A1 | 9/2014 |

OTHER PUBLICATIONS

Chu X. et al. Preparative Isolation and Purification of Five Compounds from the Chinese Medical Herb Polygonum cuspidatum . . . J of Chromatography A 1097(1-2)33-39, Dec. 2, 2005. (Year: 2005).*
Yang, F. et al. Antifungal Activity of 40 TCMs Used Individually and in Combination for Treatment of Superficial Fungal Infections. J of Ethnopharmacology 163:88-93, Jan. 2015 (Year: 2015).*
Ban et al., "Effects of a bio-assay guided fraction from Polygonum cuspidatum root on the viability, acid production and glucosyltranferase of mutans streptococci", Fitoterapia 2010, 81, 30-34.
Chu et al., "Preparative isolation and purification of five compounds from the Chinese medicinal herb Polygonum cuspidatum Sieb. et Zucc by high-speed counter-current chromatography" J Chromatogr A 2005, 1097, 33-39.
Guggenheim et al., "In vitro effect of chlorhexidine mouth rinses on polyspecies biofilms", Schweiz Monatsschrift Fur Zahnmed 2011, 121, 432-441.
Hamada et al., "Biology, Immunology, and Cariogenicity of *Streptococcus mutans*", Microbial Rev 1980, 44, 331-384.
Horner et al., "Reduced susceptibility to chlorhexidine in staphylococci: is it increasing and does it matter?", J Antimicrob Chemother 2012, 67, 2547-2559.
Jenkins et al., "The mechanism of action of chlorhexidine a study of plaque growth on enamil inserts in vivo", J Clin Periodontal, 1988, 15, 415-424.
Loesche, "Role of *Streptococcus mutans* in Human Dental Decay", Microbiol Rev 1986, 50, 353-380.

(Continued)

*Primary Examiner* — Ralph J Gitomer
(74) *Attorney, Agent, or Firm* — Riverside Law LLP

(57) ABSTRACT

The present invention describes extracts of *Polygonum cuspidatum* and related compositions that are capable of photodynamic inactivation (PDI) of microorganisms such as bacteria, viruses, fungi, and protozoa, and capable of killing or inactivating cancer cells. The present invention further describes methods of using said *Polygonum cuspidatum* extracts and photodynamic inactivation (PDI) as a therapy for the treatment of microbial infection and as well as the use of *Polygonum cuspidatum* extract and related compositions as photodynamic therapy agents for the treatment of cancer.

19 Claims, 15 Drawing Sheets

(56) References Cited

OTHER PUBLICATIONS

Song et al., "In vitro effects of a fraction separated from Polygonum cuspidatum root on the viability, in suspension and biofilms, and biofilm formation of mutans streptococci", J. Ethnopharmacol 2007, 112, 419-425.

Song et al., "In vitro inhibitory effects of Polygonum cuspidatum on bacterial viability and virulence factors of *Streptococcus mutans* and *Streptococcus sobrinus*", Arch Oral Biol 2006, 51, 1131-1140.

Suvarna, "Clinical Roundup: Selected Treatment Options for Lyme Disease", Altern Complement Ther 2012, 18, 220-225.

Kim Y-S et al: "Volatile constituents from the leaves of Polygonum cuspidatum S. et Z. and their anti-bacterial activities", Food Microbiology, Academic Press Ltd, London. GB. vol. 22, No. 1. Jan. 2005 (Jan. 1, 2005), pp. 139-144.

Lavrentieva L.V. et al. Excilamps UV radiation bactericide action on pure microorganism cultures// Tomsk State University Bulletin. Biology, 2008).

Sanarova E.V. et al. Photodynamic therapy is a way to improve the selectivity and efficiency of the tumor treatment// Russian Biotherapy Journal, 2014, pp. 110-115.

Shan et al: "Antibacterial properties of Polygonum cuspidatum roots and their major bioactive constituents", Food Chemistry, Elsevier Ltd. NL, vol. 109. No. 3, Jan. 11, 2008 (Jan. 11, 2008), pp. 530-537.

Shin JA et al. Apoptotic effect of Polygonum Cuspidatum in oral cancer cells through the regulation of specificity protein 1 //Oral Dis, Mar. 2011, 17(2)162-70, PMID:20659264, abstract.

Song J H et al: "In vitro inhibitory effects of Polygonum cuspidatum on bacterial viability and virulence factors of *Streptococcus mutans* and *Streptococcus sobrinus*", Archives of Oral Biology, Pergamon Press, Oxford, GB, vol. 51. No. 12. Dec. 1, 2006 (Dec. 1, 2006). pp. 1131-1140.

Tuchina E.S. et al. Photodynamic effect of red radiation (625 nm) and infrared radiation (805 nm) on P.Acnes bacteria treated with photosensitizers// Saratov University Proceedings, 2008, vol. 8, series: Physics, issue 1, pp. 21-26).

Ban, et al., Fitoterapia, 2010, vol. 81, pp. 30-34.

Taraszkiewicz, et al., BioMed Research International, 2013, Article ID 150653, pp. 1-13.

Inoue, et al., Journal of the Society of Synthetic Organic Chemistry, Japan, 1974, vol. 32, No. 5, pp. 348-361.

Vargas, et al., Pharmazie, 2002, vol. 57, pp. 399-404.

\* cited by examiner

POLYGONUM CUSPIDATUM EXTRACTS AS PHOTODYNAMIC INACTIVATING AGENTS

CROSS-REFERENCE TO RELATED APPLICATIONS

This application is a divisional application of U.S. patent application Ser. No. 15/282,118, filed Sep. 30, 2016, which claims priority from U.S. Provisional Patent Application Ser. No. 62/236,114, filed Oct. 1, 2015, the entire contents of which is incorporated herein by reference.

BACKGROUND OF THE INVENTION

*Polygonum cuspidatum* (*P. cuspidatum*) is a perennial plant species characterized by spreading rhizomes, reddish-brown stems, petioled leaves, and white flowers in drooping panicles. Well-known as a traditional Chinese medicine and officially listed in the Chinese Pharmacopoeia, the root of *P. cuspidatum* and its extract have been used in East Asian herbal medicine to treat conditions such as inflammatory diseases, hepatitis, tumors, menoxenia, diarrhea, skin burn, gallstones, and osteomyelitis (Ban, S. H. et al. Fitoterapia 2010, 81, 30-34. Song, J. H. et. al. J. Ethnopharmacol 2007, 112, 419-425. Chu, X. et. al. J Chromatogr A 2005, 1097, 33-39). *P. cuspidatum* originated in China where it is called Hu Zhang (H Z), or Hu Chang, and then migrated to Japan, where it is known as Kojo Kon. Today, *P. cuspidatum* can be found growing throughout North America as a tenacious weed referred to as Japanese knotweed (JK), Mexican bamboo (MB), or Japanese bamboo (JB). Although *P. cuspidatum* is viewed as an invasive species and generally regarded as a nuisance in North America, there has been some interest in its therapeutic properties for conditions such as Lyme disease (Suvarna R. Altern Complement Ther 2012, 18, 220-5).

The root of *P. cuspidatum* has been used in Korea to maintain oral hygiene and to control oral diseases, particularly biofilm-related diseases. These traditional uses have prompted several recent studies have aimed at delineating the effects of *P. cuspidatum* extracts on the viability and virulence factors of *Streptococcus mutans* and *Streptococcus sobrinus* in planktonic cultures and growing on hydroxyapatite (HA) discs (Song, J. H. et. al. Arch Oral Biol 2006, 51, 1131-1140), two species of mutans streptococci that have been implicated as important etiologic determinants of dental caries (Loesche, W. J. Microbiol Rev 1986, 50, 353-380. Hamada, S.; Slade, H. D. Microbiol Rev 1980, 44, 331-384). In these studies, certain *P. cuspidatum* extracts exhibited a broad antibacterial concentration profile, between 0.5 and 4 mg mL$^{-1}$ MIC (MIC=minimum inhibitory concentration), with MBCs (MBC=minimum bactericidal concentration) two to four times higher, against a variety of *S. mutans* and *S. sobrinus* strains in suspension. However, it took at least 8 hours post-treatment to achieve a 3-log reduction in antimicrobial activity, with $10^3$ CFU mL$^{-1}$ remaining (CFU=colony forming units). This time-dependent bacteriostatic and bactericidal activity extended to biofilms, but was attenuated substantially as expected for the more resilient form. Maximum log reductions were only 2-fold, depended on exposure and sampling time, and were heavily influenced by the thickness of the biofilm. While these findings offer proof-of-concept that *P. cuspidatum* extracts can reduce bacterial load in planktonic cultures and thin biofilms growing on hydroxyapatite (HA) discs, the magnitude of the antimicrobial effect is far less than that of the gold-standard, broad-spectrum antibiotic chlorhexidine (CHX). Moreover, the time-dependence of *P. cuspidatum* root antimicrobial action diminishes its power in the oral cavity, where substantivity is crucial. Chlorhexidine provides potent bactericidal activity and a prolonged bacteriostatic effect due to favorable adsorption properties and excellent substantivity, ideal qualities of oral antimicrobials that few products meet (Jenkins, S. et. al. J Clin Periodontol, 1988, 15, 415-424). Unfortunately, chlorhexidine preparations stain teeth, alter taste perception, and are generally indicated for short-term use (Guggenheim, B.; Meier A. Schweiz Monatsschrift Für Zahnmed 2011, 121, 432-441). These factors, alongside concerns over the widespread use of antibiotics and the development of antibiotic resistance (Homer, C. et. al. J Antimicrob Chemother 2012, 67, 2547-2559), warrant new strategies that are potent, fast-acting or highly substantive, and broad-spectrum in relation to bacterial targets and mechanism(s) of action.

Photodynamic inactivation (PDI) of microorganisms represents a powerful alternative to traditional antibiotics, exceeding these criteria. Briefly, PDI employs a photosensitizer (PS), light, and oxygen to inactivate and destroy bacteria, viruses, fungi, and protozoa through the production of cytotoxic singlet oxygen ($^1O_2$), and other reactive oxygen species (ROS), from an excited state of the photosensitizer. The onset of the photodynamic effect is instant, thus PDI is immediate, and its mechanism of action is nonspecific. Consequently, there are no reports of antibiotic resistance to a toxic burst of ROS. The immediate response eliminates the need for antimicrobials with high substantivity for prolonged action in the oral cavity. Selectivity is an inherent property of PDI, whereby activity is confined to regions where extract, light, and oxygen overlap in space and time. Therefore, healthy tissue can be spared by controlling where light is shone.

The concept of PDI represents a general method of killing cells that can also be applied in the treatment of cancer. When used on cancer cells and tumors, the process is termed photodynamic therapy (PDT). As with the photodynamic inactivation of microorganisms, PDT employs a photosensitizer (PS), light, and oxygen to inactivate and destroy cancer cells and tumors through the production of cytotoxic singlet oxygen ($^1O_2$), and other reactive oxygen species (ROS), from an excited state of the photosensitizer.

There remains a need in the art for novel compositions and formulations with bactericidal or anti-cancer activity, and methods of making and using the same, in particular methods including photodynamic inactivation and photodynamic therapy using compositions and formulations with bactericidal or anti-cancer activity. This invention fulfills these needs.

SUMMARY OF THE INVENTION

In one aspect, the present invention relates to a method of killing or inactivating microorganisms, the method comprising the steps of contacting the microorganisms with a composition comprising an extract of *Polygonum cuspidatum* and an excipient; and irradiating the microorganisms with a source of light. In one embodiment, the method is performed in the presence of oxygen. In one embodiment, the microorganisms are in the oral cavity of a subject. In one embodiment, the microorganisms are part of a biofilm. In one embodiment, the microorganisms are attached to a dental appliance. In one embodiment, the dental appliance is selected from the group consisting of orthodontic brackets, bands, buttons, bonded attachments, bonded wire, crowns, inlays, onlays, restorations, dental abutments, and dental implants. In one embodiment, the microorganisms are selected from the group consisting of as bacteria, viruses, fungi, and protozoa. In one embodiment, the microorganisms are on the surface of a tooth, in the a cavity in a tooth, on the surface of the gums, or on the mandibular or maxillary arches.

In one embodiment, the radiant exposure of the light is between 1 and 300 J cm$^{-2}$, and the surface power density of the light is between 0.001 and 0.25 W cm$^{-2}$. In one embodiment, the source of light is selected from the group consisting of a source of visible light, a source of blue light, a source of green light, and a source of ultraviolet light. In one embodiment, wherein the light has a wavelength between 400 nm and 700 nm.

In one embodiment, the composition is formulated as a formulation selected from the group consisting of a solution, a suspension, a paste, a gel, and a foam. In one embodiment, the excipient is selected from the group consisting of an abrasive, a detergent, a binding agent, a humectant, a flavoring agent, a sweetening agent, a coloring agent, a preservative, and water. In one embodiment, the excipient is selected from the group consisting of water, silica, sorbitol, glycerin, xylitol, a coco sulfate salt, decyl glucoside, a flavoring agent, xanthan gum, carrageenan, and a glutamate. In one embodiment, the percentage of *Polygonum cuspidatum* extract in the composition is between 0.01 and 20%. In one embodiment, the percentage of *Polygonum cuspidatum* extract in the composition is about 1%. In one embodiment, the extract of *Polygonum cuspidatum* comprises at least one of emodin, physicion, rhein, and glycosylated derivatives thereof. In one embodiment, the extract of of *Polygonum cuspidatum* comprises 0.51-0.65% emodin by weight. In one embodiment, the composition comprising an extract of *Polygonum cuspidatum* and an excipient comprises between 0.1% and 10% *Polygonum cuspidatum* extract; between 20% and 45% abrasives; between 1% and 2% detergent; between 0.5% and 4% binding agents; between 10% and 30% humectants; between 1% and 5% flavoring, sweetening, and coloring agents; and between 0.05% and 0.5% preservatives.

The present invention also relates in part to a method of treating or preventing a microbial infection in a subject, the method comprising the step of administering to a subject an effective amount of one or more extracts of *Polygonum cuspidatum* in the presence of light and oxygen.

DETAILED DESCRIPTION OF THE INVENTION

Figure 1:
FIG. 1: Treatment of common soil bacteria with *P. cuspidatum* extract (100 μg) in the dark (left) and with light activation (right). The light treatment was 35 J cm$^{-2}$ of light from a photoreactor. The light source delivers 0.0096 W cm$^{-2}$ to the sample surface.
Figure 2:
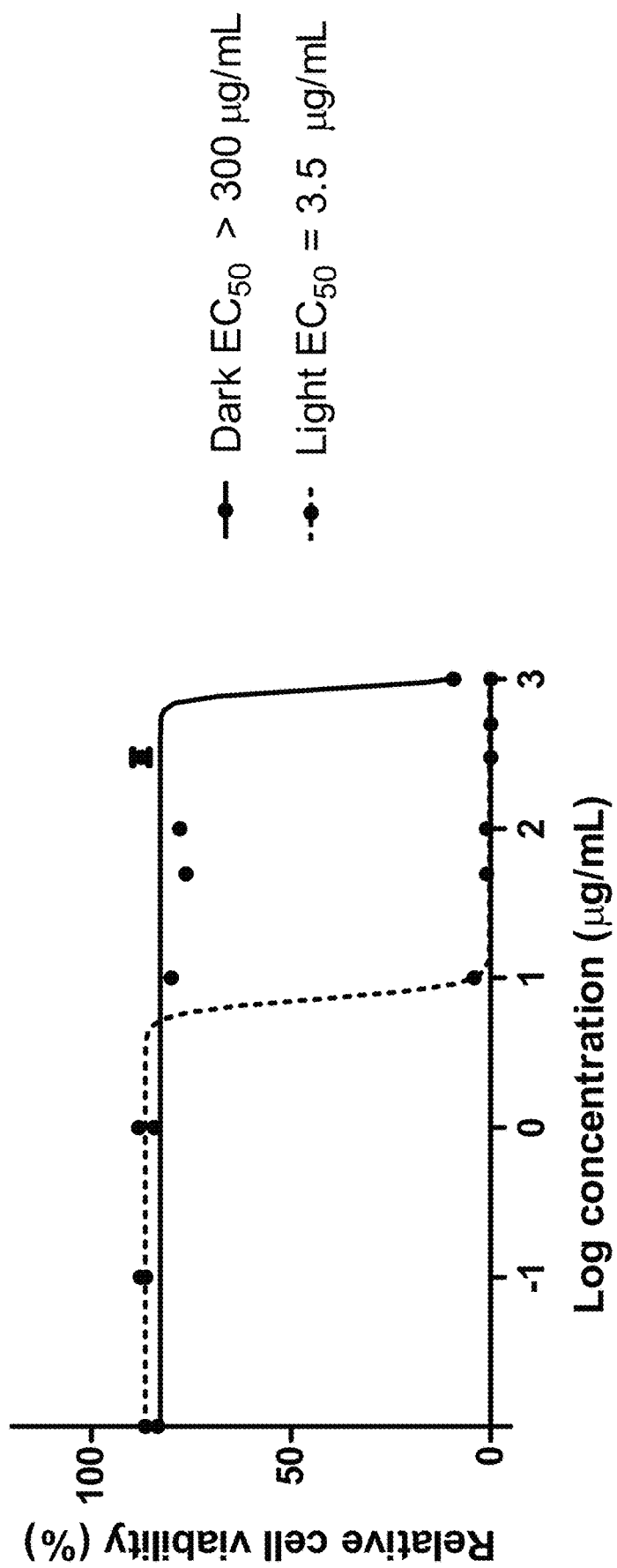
FIG. 2: PDT treatment of human leukemia cancer cells with *P. cuspidatum* extract in the dark (solid curve) and with light activation (dashed curve). The light treatment was 28 J cm$^{-2}$ of light from a photoreactor.

The present invention is directed toward novel extracts of *Polygonum cuspidatum* that are capable of photodynamic inactivation of microorganisms such as bacteria, viruses, fungi, and protozoa. The novel *Polygonum cuspidatum* extracts of the present invention are capable of photodynamic inactivation of microorganisms such as bacteria, viruses, and fungi in the presence of light. Further, the *Polygonum cuspidatum* extracts that are capable of photodynamic inactivation of microorganisms according to the present invention are useful for killing said microorganism in the presence of light. In addition, said *Polygonum cuspidatum* extracts that are capable of photodynamic inactivation of microorganisms are useful for the treatment of microorganism infection in a subject by administration of said *Polygonum cuspidatum* extracts that are capable of photodynamic inactivation of microorganisms to a subject in need in the presence of light and oxygen.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures are those well-known and commonly employed in the art, and standard techniques or modifications thereof are used.

The articles "a" and "an" are used herein to refer to one or to more than one, i.e., to at least one of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "or," as used herein, means "and/or" unless explicitly indicated to refer to alternatives only or the alternatives are mutually exclusive, although the disclosure supports a definition that refers to only alternatives and "and/or."

The terms "inhibiting," "reducing," or "preventing," "diminishing," and variations of these terms, as used herein include any measurable decrease, including complete or substantially complete inhibition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as animals such as rabbits, rats, mice, dogs, cats, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

Throughout this disclosure, various aspects of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

As used herein, non-limiting examples of bacteria include *Helicobacter pylori, Legionella pneumophilia, Mycobacterium tuberculosis, Mycobacterium avium, Mycobacterium intracellulare, Mycobacterium kansaii, Mycobacterium gordonae, Mycobacteria sporozoites, Staphylococcus aureus, Staphylococcus epidermidis, Neisseria gonorrhoeae, Neisseria meningitidis, Listeria monocytogenes, Streptococcus pyogenes* (Group A *Streptococcus*), *Streptococcus agalactiae pyogenes* (Group B *Streptococcus*), *Streptococcus dysgalactia, Streptococcus faecalis, Streptococcus bovis, Streptococcus pneumoniae,* pathogenic *Campylobacter sporozoites, Enterococcus sporozoites, Haemophilus influenzae, Pseudomonas aeruginosa, Bacillus anthracia, Bacillus subtilis, Escherichia coli, Corynebacterium diphtheriae, Corynebacterium jeikeium, Corynebacterium sporozoites, Erysipelothrix rhusiopathiae, Clostridium perfringens, Clostridium tetani, Clostridium difficile, Enterobacter aerogenes, Klebsiella pneumoniae, Pasturella multocida, Bacteroides thetaiotamicron, Bacteroides uniformis, Bacteroides vulgatus, Fusobacterium nucleatum, Streptobacillus monili-* formis, Leptospira, Actinomyces israelli. Steptococcus galactiae, Streptococcus mutans, Streptococcus sobrinus, lactobacilli such as Lactobacillus acidophilus, Actinomyces spp., Nocardia spp., A. actinomycetemcomitans, P. gingivalis, P. intermedia, B. forsythus, C. rectus, E. nodatum, P. micros, S. intermedius, Treponema sp., Methicillin Resistant Staphylococcus aureus (MRSA) and Vancomycin Resistant Entercocci (VRE).

As used herein, non-limiting examples of viruses include Retroviridae (e.g., human immunodeficiency viruses, such as HIV-1 (also referred to as HTLV-III, LA V or HTLV-III/LAV), or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses, severe acute respiratory syndrome (SARS) virus); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (e.g., Hepatitis B virus); Parvoviridae (parvoviruses); Papovaviridae (papilloma viruses, polyoma viruses); Adenoviridae (most adenoviruses); Herpesviridae (e.g., herpes simplex virus (HSV) 1 and 2, varicella zoster virus, cytomegalovirus (CMV), herpes viruses); Poxviridae (e.g., variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parentally transmitted, i.e., Hepatitis C); Norwalk and related viruses, and astroviruses).

As used herein, non-limiting examples of fungi include Cryptococcus neoformans, Histoplasma capsulatum, Coccidioides immitis, Blastomyces dermatitidis, Chlamydia trachoma tis, Candida albicans, Candida tropicaiis, Candida glabrata, Candida krusei, Candida parapsilosis, Candida dubliniensis, Candida lusitaniae, Epidermophyton floccosum, Microsporum audouinii, Microsporum canis, Microsporum canisvar. distortum Microsporum cookei, Microsporum equinum, Microsporum ferrugineum, Microsporum fulvum, Microsporum gallinae, Microsporum gypseum, Microsporum nanum, Microsporum persicolor, Trichophyton ajelioi, Trichophyton concentricum, Trichophyton equinum, Trichophyton flavescens, Trichophyton gioriae, Trichophyton megnini, Trichophyton mentagrophytes var. erinacei, Trichophyton mentagrophytes var. interdigitale, Trichophyton phaseoliforme, Trichophyton rub rum, Trichophyton rub rum downy strain, Trichophyton rubrum granular strain, Trichophyton schoenleinii, Trichophyton simii, Trichophyton soudanense, Trichophyton terrestre, Trichophyton tonsurans, Trichophyton vanbreuseghemii, Trichophyton verrucosum, Trichophyton violaceum, Trichophyton yaoundei, Aspergillus fumigatus, Aspergillus flavus, and Aspergillus clavatus.

As used herein, non-limiting examples of protozoa include Trichomonas vaginalis, Giardia lamblia, Entamoeba histolytica, Balantidium coli, Cryptosporidium parvum and Isospora belli, Trypanosoma cruzi, Trypanosoma gambiense, Leishmania donovani, and Naegleria fowleri.

As used herein, non-limiting examples of cancer cells, carcinomas and tumors include leukemia cells and tumors, melanoma cells and tumors, basal cell carcinomas, squamous cell carcinomas, verrucous carcinomas, minor salivary gland carcinomas, lymphomas, adenoid cystic cancer cells and tumors, bladder cells and tumors, breast cells and tumors, and colon cancer cells and tumors.

As used herein, non-limiting examples of benign oral cavity and oropharyngeal tumors includes eosinophilic granulomas, fibromas, granular cell tumors, karatoacanthomas, leiomyomas, osteochondromas, lipomas, schwannomas, neurofibromas, papillomas, condyloma acuminatums, verruciform xanthoma, pyogenic granulomas, rhabdomyoma, and odontogenic tumors.

The materials, methods, and examples provided below provide representative methods for preparing exemplary P. cuspidatum extracts of the present invention. The materials, methods, and examples provided below further provide representative methods of demonstrating the ability of P. cuspidatum extracts to provide photodynamic inactivation (PDI) of microorganisms such as bacteria, viruses, fungi, and protozoa. The skilled practitioner will know how to substitute the appropriate reagents, starting materials and purification methods known to those skilled in the art, in order to prepare the P. cuspidatum extracts of the present invention and to demonstrate the ability of the P. cuspidatum extracts to provide photodynamic inactivation (PDI) of microorganisms such as bacteria, viruses, fungi, and protozoa.

Description

The present invention is directed toward novel extracts of Polygonum cuspidatum that are capable of photodynamic inactivation of bacteria selected from the group consisting of Helicobacter pylori, Legionella pneumophilia, Mycobacterium tuberculosis, Mycobacterium avium, Mycobacterium intracellulare, Mycobacterium kansaii, Mycobacterium gordonae, Mycobacteria sporozoites, Staphylococcus aureus, Staphylococcus epidermidis, Neisseria gonorrhoeae, Neisseria meningitidis, Listeria monocytogenes, Streptococcus pyogenes (Group A Streptococcus), Streptococcus agalactiae pyogenes (Group B Streptococcus), Streptococcus dysgalactia, Streptococcus faecalis, Streptococcus bovis, Streptococcus pneumoniae, pathogenic Campylobacter sporozoites, Enterococcus sporozoites, Haemophilus influenzae, Pseudomonas aeruginosa, Bacillus anthracia, Bacillus subtilis, Escherichia coli, Corynebacterium diphtheriae, Corynebacterium jeikeium, Corynebacterium sporozoites, Erysipelothrix rhusiopathiae, Clostridium perfringens, Clostridium tetani, Clostridium difficile, Enterobacter aerogenes, Klebsiella pneumoniae, Pasturella multocida, Bacteroides thetaiotamicron, Bacteroides uniformis, Bacteroides vulgatus, Fusobacterium nucleatum, Streptobacillus moniliformis, Leptospira, Actinomyces israelli. Steptococcus galactiae, Streptococcus mutans, Streptococcus sobrinus, lactobacilli such as Lactobacillus acidophilus, Actinomyces spp., Nocardia spp., A. actinomycetemcomitans, P. gingivalis, P. intermedia, B. forsythus, C. rectus, E. nodatum, P. micros, S. intermedius, Treponema sp., Methicillin Resistant Staphylococcus aureus (MRSA) and Vancomycin Resistant Entercocci (VRE).

The present invention is directed toward novel extracts of Polygonum cuspidatum that are capable of photodynamic inactivation of viruses selected from the group consisting of Retroviridae (e.g., human immunodeficiency viruses, such as HIV-1 (also referred to as HTLV-III, LA V or HTLV-III/

LAV), or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses, severe acute respiratory syndrome (SARS) virus); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (e.g., Hepatitis B virus); Parvoviridae (parvoviruses); Papovaviridae (papilloma viruses, polyoma viruses); Adenoviridae (most adenoviruses); Herpesviridae (e.g., herpes simplex virus (HSV) 1 and 2, varicella zoster virus, cytomegalovirus (CMV), herpes viruses); Poxviridae (e.g., variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parentally transmitted, i.e., Hepatitis C); Norwalk and related viruses, and astroviruses).

The present invention is directed toward novel extracts of *Polygonum cuspidatum* that are capable of photodynamic inactivation of fungi selected from the group consisting of *Cryptococcus neoformans, Histoplasma capsulatum, Coccidioides immitis, Blastomyces dermatitidis, Chlamydia trachoma tis, Candida albicans, Candida tropicaiis, Candida glabrata, Candida krusei, Candida parapsilosis, Candida dubliniensis, Candida lusitaniae, Epidermophyton floccosum, Microsporum audouinii, Microsporum canis, Microsporum canisvar. distortum Microsporum cookei, Microsporum equinum, Microsporum ferrugineum, Microsporum fulvum, Microsporum gallinae, Microsporum gypseum, Microsporum nanum, Microsporum persicolor, Trichophyton ajelioi, Trichophyton concentricum, Trichophyton equinum, Trichophyton flavescens, Trichophyton gioriae, Trichophyton megnini, Trichophyton mentagrophytes* var. erinacei, *Trichophyton mentagrophytes* var. interdigitale, *Trichophyton phaseoliforme, Trichophyton rubrum, Trichophyton rubrum* downy strain, *Trichophyton rubrum* granular strain, *Trichophyton schoenleinii, Trichophyton simii, Trichophyton soudanense, Trichophyton terrestre, Trichophyton tonsurans, Trichophyton vanbreuseghemii, Trichophyton verrucosum, Trichophyton violaceum, Trichophyton yaoundei, Aspergillus fumigatus, Aspergillus flavus,* and *Aspergillus clavatus.*

The present invention is directed toward novel extracts of *Polygonum cuspidatum* that are capable of photodynamic inactivation of protozoa selected from the group consisting of *Trichomonas vaginalis, Giardia lamblia, Entamoeba histolytica, Balantidium coli, Cryptosporidium parvum* and *Isospora belli, Trypanosoma cruzi, Trypanosoma gambiense, Leishmania donovani,* and *Naegleria fowleri.*

The present invention is further directed toward novel extracts of *Polygonum cuspidatum* that are useful as photodynamic therapy agents capable of killing cancer cells, carcinomas and tumors.

The present invention is further directed toward novel extracts of *Polygonum cuspidatum* that are useful as photodynamic therapy agents capable of killing cancer cells, carcinomas and tumors selected from the group consisting of leukemia cells and tumors, melanoma cells and tumors, basal cell carcinomas, squamous cell carcinomas, verrucous carcinomas, minor salivary gland carcinomas, lymphomas, adenoid cystic cancer cells and tumors, bladder cells and tumors, breast cells and tumors, and colon cancer cells and tumors.

The present invention is further directed toward novel extracts of *Polygonum cuspidatum* that are useful as photodynamic therapy agents capable of treating benign oral cavity and oropharyngeal tumors.

The present invention is further directed toward novel extracts of *Polygonum cuspidatum* that are useful as photodynamic therapy agents capable of treating benign oral cavity and oropharyngeal tumors selected from the group consisting of eosinophilic granulomas, fibromas, granular cell tumors, karatoacanthomas, leiomyomas, osteochondromas, lipomas, schwannomas, neurofibromas, papillomas, condyloma acuminatums, verruciform xanthoma, pyogenic granulomas, rhabdomyoma, and odontogenic tumors.

The present invention further relates to compositions comprising an effective amount of one or more extracts of *Polygonum cuspidatum* that are capable of photodynamic inactivation of microorganisms according to the present invention and an excipient.

The present invention further relates to a method of killing microorganisms such as bacteria, viruses, fungi, and protozoa, said method comprising contacting said microorganism with one or more extracts of *Polygonum cuspidatum* that are capable of photodynamic inactivation of microorganisms according to the present invention in the presence of light and oxygen.

The present invention further relates to a method of killing microorganisms such as bacteria, viruses, fungi, and protozoa, said method comprising contacting said microorganism with one or more extracts of *Polygonum cuspidatum* that are capable of photodynamic inactivation of microorganisms according to the present invention and an excipient in the presence of light and oxygen.

The present invention further relates to a method of treating a microbial infection in a subject such as infection with a bacteria, viruses, fungi, and protozoa, said method comprising administering to a subject an effective amount of one or more extracts of *Polygonum cuspidatum* that are capable of photodynamic inactivation of microorganisms according to the present invention in the presence of light and oxygen.

The present invention further relates to a method of treating a microbial infection in a subject such as infection with a bacteria, viruses, fungi, and protozoa, said method comprising administering to a subject an effective amount of one or more extracts of *Polygonum cuspidatum* that are capable of photodynamic inactivation of microorganisms according to the present invention and an excipient in the presence of light and oxygen.

The present invention further relates to a method of treating a microbial infection in the oral cavity of a subject such as infection with a bacteria, viruses, fungi, and protozoa, said method comprising administering to the oral cavity of a subject an effective amount of one or more extracts of *Polygonum cuspidatum* that are capable of photodynamic inactivation of microorganisms according to the present invention in the presence of light and oxygen.

The present invention further relates to a method of treating a microbial infection in the oral cavity of a subject such as infection with a bacteria, viruses, fungi, and protozoa, said method comprising administering to a to the oral cavity of subject an effective amount of one or more extracts of *Polygonum cuspidatum* that are capable of photodynamic inactivation of microorganisms according to the present invention and an excipient in the presence of light and oxygen.

The present invention further relates to a method of eliminating a biofilm in the oral cavity of a subject wherein the biofilm contains bacteria, viruses, fungi, and protozoa, said method comprising administering to the oral cavity of a subject an effective amount of one or more extracts of *Polygonum cuspidatum* that are capable of photodynamic inactivation of microorganisms according to the present invention in the presence of light and oxygen.

The present invention further relates to a method of eliminating a biofilm in the oral cavity of a subject wherein the biofilm contains bacteria, viruses, fungi, and protozoa, said method comprising administering to the oral cavity of a subject an effective amount of one or more extracts of *Polygonum cuspidatum* that are capable of photodynamic inactivation of microorganisms according to the present invention and an excipient in the presence of light and oxygen.

The present invention further relates to a method of preventing the formation of a biofilm in the oral cavity of a subject wherein the biofilm contains bacteria, viruses, fungi, and protozoa, said method comprising administering to the oral cavity of a subject an effective amount of one or more extracts of *Polygonum cuspidatum* that are capable of photodynamic inactivation of microorganisms according to the present invention in the presence of light and oxygen.

The present invention further relates to a method of preventing the formation of a biofilm in the oral cavity of a subject wherein the biofilm contains bacteria, viruses, fungi, and protozoa, said method comprising administering to the oral cavity of a subject an effective amount of one or more extracts of *Polygonum cuspidatum* that are capable of photodynamic inactivation of microorganisms according to the present invention and an excipient in the presence of light and oxygen.

The present invention further relates to a method of lowering the microbial load in the oral cavity of a subject, said method comprising administering to the oral cavity of a subject an effective amount of one or more extracts of *Polygonum cuspidatum* that are capable of photodynamic inactivation of microorganisms according to the present invention in the presence of light and oxygen.

The present invention further relates to a method of lowering the microbial load in the oral cavity of a subject, said method comprising administering to the oral cavity of a subject an effective amount of one or more extracts of *Polygonum cuspidatum* that are capable of photodynamic inactivation of microorganisms according to the present invention and an excipient in the presence of light and oxygen.

The present invention further relates to a method of treating a microbial infection on the surface of a tooth such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen.

The present invention further relates to a method of treating a microbial infection on the surface of a tooth such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of treating a microbial infection on the surface of a tooth such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen.

The present invention further relates to a method of treating a microbial infection on the surface of a tooth such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of preventing a microbial infection on the surface of a tooth such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen.

The present invention further relates to a method of preventing a microbial infection on the surface of a tooth such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of preventing a microbial infection on the surface of a tooth such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen.

The present invention further relates to a method of preventing a microbial infection on the surface of a tooth such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of lowering the microbial load on the surface of a tooth such, said method comprising administering to a tooth surface an effective amount of one or more extracts of *Polygonum cuspidatum* that are capable of photodynamic inactivation of microorganisms according to the present invention in the presence of light and oxygen.

The present invention further relates to a method of lowering the microbial load on the surface of a tooth such, said method comprising administering to a tooth surface an effective amount of one or more extracts of *Polygonum cuspidatum* that are capable of photodynamic inactivation of microorganisms according to the present invention in the presence of light and oxygen wherein the said surface of a tooth is selected from the lingual, occlusal, proximal, and buccal surfaces of the posterior teeth, and the lingual, incisal, proximal, and labial surfaces of the anterior teeth.

The present invention further relates to a method of lowering the microbial load on the surface of a tooth such, said method comprising administering to a tooth surface an effective amount of one or more extracts of *Polygonum cuspidatum* that are capable of photodynamic inactivation of microorganisms according to the present invention and an excipient in the presence of light and oxygen.

The present invention further relates to a method of lowering the microbial load on the surface of a tooth such, said method comprising administering to a tooth surface an effective amount of one or more extracts of *Polygonum cuspidatum* that are capable of photodynamic inactivation of microorganisms according to the present invention and an excipient in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of eliminating a biofilm on the surface of a tooth wherein the biofilm contains bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen.

The present invention further relates to a method of eliminating a biofilm on the surface of a tooth wherein the biofilm contains bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of eliminating a biofilm on the surface of a tooth wherein the biofilm contains bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen.

The present invention further relates to a method of eliminating a biofilm on the surface of a tooth wherein the biofilm contains bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of preventing the formation of a biofilm on the surface of a tooth wherein the biofilm contains bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen.

The present invention further relates to a method of preventing the formation of a biofilm on the surface of a tooth wherein the biofilm contains bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of preventing the formation of a biofilm on the surface of a tooth wherein the biofilm contains bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen.

The present invention further relates to a method of preventing the formation of a biofilm on the surface of a tooth wherein the biofilm contains bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen wherein the said surface of a tooth is selected from the group consisting of the lingual, occlusal, proximal, and buccal surfaces of the posterior teeth, and the lingual, incisal, proximal, and labial surfaces of the anterior teeth.

The present invention further relates to a method of treating a cavity in a tooth, said method comprising administering to a tooth an effective amount of one or more extracts of *Polygonum cuspidatum* that are capable of photodynamic inactivation of microorganisms according to the present invention in the presence of light and oxygen.

The present invention further relates to a method of treating a cavity in a tooth, said method comprising administering to a tooth an effective amount of one or more extracts of *Polygonum cuspidatum* that are capable of photodynamic inactivation of microorganisms according to the present invention and an excipient in the presence of light and oxygen.

The present invention further relates to a method of preventing cavities in a tooth, said method comprising administering to a tooth an effective amount of one or more extracts of *Polygonum cuspidatum* that are capable of photodynamic inactivation of microorganisms according to the present invention in the presence of light and oxygen.

The present invention further relates to a method of preventing cavities in a tooth, said method comprising administering to a tooth an effective amount of one or more extracts of *Polygonum cuspidatum* that are capable of photodynamic inactivation of microorganisms according to the present invention and an excipient in the presence of light and oxygen.

The present invention further relates to a method of treating a microbial infection on the surface of the gums such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen.

The present invention further relates to a method of treating a microbial infection on the surface of the gums such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen wherein the said gum surface is selected from the group consisting of the gingival margin, the sulcus, and the opening surface of a periodontal pocket.

The present invention further relates to a method of treating a microbial infection on the surface of the gums such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen.

The present invention further relates to a method of treating a microbial infection on the surface of the gums such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention and an excipient in the presence of light and oxygen where in the said gum surface is selected from the group consisting of the gingival margin, the sulcus, and the opening surface of a periodontal pocket.

The present invention further relates to a method of preventing a microbial infection on the surface of the gums such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen.

The present invention further relates to a method of preventing a microbial infection on the surface of the gums such as infection with a bacteria, viruses, fungi, and protozoa, said method comprising administering to a tooth surface an effective amount of one or more extracts of *Polygonum cuspidatum* that are capable of photodynamic inactivation of microorganisms according to the present invention in the presence of light and oxygen wherein the said gum surface is selected from the group consisting of the gingival margin, the sulcus, and the opening surface of a periodontal pocket.

The present invention further relates to a method of preventing a microbial infection on the surface of the gums such as infection with a bacteria, viruses, fungi, and protozoa, said method comprising administering to a gum surface an effective amount of one or more extracts of *Polygonum cuspidatum* that are capable of photodynamic inactivation of microorganisms according to the present invention and an excipient in the presence of light and oxygen.

The present invention further relates to a method of preventing a microbial infection on the surface of the gums such as infection with a bacteria, viruses, fungi, and protozoa, said method comprising administering to a gum surface an effective amount of one or more extracts of *Polygonum cuspidatum* that are capable of photodynamic inactivation of microorganisms according to the present invention and an excipient in the presence of light and oxygen wherein the said gum surface is selected from the group consisting of the gingival margin, the sulcus, and the opening surface of a periodontal pocket.

The present invention further relates to a method of lowering the microbial load on the surface of the gums such, said method comprising administering to a gum surface an effective amount of one or more extracts of *Polygonum cuspidatum* that are capable of photodynamic inactivation of microorganisms according to the present invention in the presence of light and oxygen.

The present invention further relates to a method of lowering the microbial load on the surface of the gums such, said method comprising administering to a gum surface an effective amount of one or more extracts of *Polygonum cuspidatum* that are capable of photodynamic inactivation of microorganisms according to the present invention in the presence of light and oxygen wherein the said gum surface is selected from the group consisting of the gingival margin, the sulcus, and the opening surface of a periodontal pocket.

The present invention further relates to a method of lowering the microbial load on the surface of the gums such, said method comprising administering to a gum surface an effective amount of one or more extracts of *Polygonum cuspidatum* that are capable of photodynamic inactivation of microorganisms according to the present invention and an excipient in the presence of light and oxygen.

The present invention further relates to a method of lowering the microbial load on the surface of the gums such, said method comprising administering to a gum surface an effective amount of one or more extracts of *Polygonum cuspidatum* that are capable of photodynamic inactivation of microorganisms according to the present invention and an excipient in the presence of light and oxygen wherein the said gum surface is selected from the group consisting of the gingival margin, the sulcus, and the opening surface of a periodontal pocket.

The present invention further relates to a method of eliminating a biofilm on the surface of the gums wherein the biofilm contains bacteria, viruses, fungi, and protozoa, said method comprising administering to a gum surface an effective amount of one or more extracts of *Polygonum cuspidatum* that are capable of photodynamic inactivation of microorganisms according to the present invention in the presence of light and oxygen.

The present invention further relates to a method of eliminating a biofilm on the surface of the gums wherein the biofilm contains bacteria, viruses, fungi, and protozoa, said method comprising administering to a gum surface an effective amount of one or more extracts of *Polygonum cuspidatum* that are capable of photodynamic inactivation of microorganisms according to the present invention in the presence of light and oxygen wherein the said gum surface is selected from the group consisting of the gingival margin, the sulcus, and the opening surface of a periodontal pocket.

The present invention further relates to a method of eliminating a biofilm on the surface of the gums wherein the biofilm contains bacteria, viruses, fungi, and protozoa, said method comprising administering to a gum surface an effective amount of one or more extracts of *Polygonum cuspidatum* that are capable of photodynamic inactivation of microorganisms according to the present invention and an excipient in the presence of light and oxygen.

The present invention further relates to a method of eliminating a biofilm on the surface of the gums wherein the biofilm contains bacteria, viruses, fungi, and protozoa, said method comprising administering to a gum surface an effective amount of one or more extracts of *Polygonum cuspidatum* that are capable of photodynamic inactivation of microorganisms according to the present invention and an excipient in the presence of light and oxygen wherein the said gum surface is selected from the group consisting of the gingival margin, the sulcus, and the opening surface of a periodontal pocket.

The present invention further relates to a method of preventing the formation of a biofilm on the surface of the gums wherein the biofilm contains bacteria, viruses, fungi, and protozoa, said method comprising administering to a gum surface an effective amount of one or more extracts of *Polygonum cuspidatum* that are capable of photodynamic inactivation of microorganisms according to the present invention in the presence of light and oxygen.

The present invention further relates to a method of preventing the formation of a biofilm on the surface of the gums wherein the biofilm contains bacteria, viruses, fungi, and protozoa, said method comprising administering to a gum surface an effective amount of one or more extracts of *Polygonum cuspidatum* that are capable of photodynamic inactivation of microorganisms according to the present invention in the presence of light and oxygen wherein the said gum surface is selected from the group consisting of the gingival margin, the sulcus, and the opening surface of a periodontal pocket.

The present invention further relates to a method of eliminating a biofilm on the surface of the gums wherein the biofilm contains bacteria, viruses, fungi, and protozoa, said method comprising administering to a gum surface an effective amount of one or more extracts of *Polygonum cuspidatum* that are capable of photodynamic inactivation of microorganisms according to the present invention and an excipient in the presence of light and oxygen.

The present invention further relates to a method of eliminating a biofilm on the surface of the gums wherein the biofilm contains bacteria, viruses, fungi, and protozoa, said method comprising administering to a gum surface an effective amount of one or more extracts of *Polygonum cuspidatum* that are capable of photodynamic inactivation of microorganisms according to the present invention and an excipient in the presence of light and oxygen wherein the said gum surface is selected from the group consisting of the gingival margin, the sulcus, and the opening surface of a periodontal pocket.

The present invention further relates to a method of treating a microbial infection on the mandibular and maxillary arches, said method comprising administering to the mandibular and maxillary arches an effective amount of one or more extracts of *Polygonum cuspidatum* that are capable of photodynamic inactivation of microorganisms according to the present invention in the presence of light and oxygen.

The present invention further relates to a method of treating a microbial infection on the mandibular and maxillary arches, said method comprising administering to the mandibular and maxillary arches an effective amount of one or more extracts of *Polygonum cuspidatum* that are capable of photodynamic inactivation of microorganisms according to the present invention and an excipient in the presence of light and oxygen.

The present invention further relates to a method of preventing a microbial infection on the mandibular and maxillary arches, said method comprising administering to the mandibular and maxillary arches an effective amount of one or more extracts of *Polygonum cuspidatum* that are capable of photodynamic inactivation of microorganisms according to the present invention in the presence of light and oxygen.

The present invention further relates to a method of preventing a microbial infection on the mandibular and maxillary arches, said method comprising administering to the mandibular and maxillary arches an effective amount of one or more extracts of *Polygonum cuspidatum* that are capable of photodynamic inactivation of microorganisms according to the present invention and an excipient in the presence of light and oxygen.

The present invention further relates to a method of lowering the microbial load on the mandibular and maxillary arches, said method comprising administering to the mandibular and maxillary arches an effective amount of one or more extracts of *Polygonum cuspidatum* that are capable of photodynamic inactivation of microorganisms according to the present invention in the presence of light and oxygen.

The present invention further relates to a method of lowering the microbial load on the mandibular and maxillary arches, said method comprising administering to the mandibular and maxillary arches an effective amount of one or more extracts of *Polygonum cuspidatum* that are capable of photodynamic inactivation of microorganisms according to the present invention and an excipient in the presence of light and oxygen.

The present invention further relates to a method of eliminating a biofilm on the mandibular and maxillary arches, said method comprising administering to the mandibular and maxillary arches an effective amount of one or more extracts of *Polygonum cuspidatum* that are capable of photodynamic inactivation of microorganisms according to the present invention in the presence of light and oxygen.

The present invention further relates to a method of eliminating a biofilm on the mandibular and maxillary arches, said method comprising administering to the mandibular and maxillary arches an effective amount of one or more extracts of *Polygonum cuspidatum* that are capable of photodynamic inactivation of microorganisms according to the present invention and an excipient in the presence of light and oxygen.

The present invention further relates to a method of preventing the formation of a biofilm on the mandibular and maxillary arches, said method comprising administering to the mandibular and maxillary arches an effective amount of one or more extracts of *Polygonum cuspidatum* that are capable of photodynamic inactivation of microorganisms according to the present invention in the presence of light and oxygen.

The present invention further relates to a method of preventing the formation of a biofilm on the mandibular and maxillary arches, said method comprising administering to the mandibular and maxillary arches an effective amount of one or more extracts of *Polygonum cuspidatum* that are capable of photodynamic inactivation of microorganisms according to the present invention and an excipient in the presence of light and oxygen.

The present invention further relates to a method of killing microorganisms such as a bacteria, viruses, fungi, and protozoa, on the surface of dental appliances, said method comprising administering to a surface of a dental appliance an effective amount of one or more extracts of *Polygonum cuspidatum* that are capable of photodynamic inactivation of microorganisms according to the present invention in the presence of light and oxygen.

The present invention further relates to a method of killing microorganisms such as a bacteria, viruses, fungi, and protozoa, on the surface of dental appliances, said method comprising administering to a surface of a dental appliance an effective amount of one or more extracts of *Polygonum cuspidatum* that are capable of photodynamic inactivation of microorganisms according to the present invention in the presence of light and oxygen wherein the said dental appliance is selected from the group consisting of orthodontic brackets, bands, buttons, bonded attachments, bonded wire, crowns, inlays, onlays, restorations, dental abutments, and dental implants.

The present invention further relates to a method of killing microorganisms such as bacteria, viruses, fungi, and protozoa on the surface of dental appliances, said method comprising administering to a surface of a dental appliance an effective amount of one or more extracts of *Polygonum cuspidatum* that are capable of photodynamic inactivation of microorganisms according to the present invention and an excipient in the presence of light and oxygen.

The present invention further relates to a method of killing microorganisms such as bacteria, viruses, fungi, and protozoa on the surface of dental appliances, said method comprising administering to a surface of a dental appliance an effective amount of one or more extracts of *Polygonum cuspidatum* that are capable of photodynamic inactivation of microorganisms according to the present invention and an excipient in the presence of light and oxygen wherein the said dental appliances are selected from the group consisting of orthodontic brackets, bands, buttons, bonded attachments, bonded wire, crowns, inlays, onlays, restorations, dental abutments, and dental implants.

The present invention further relates to compositions comprising an effective amount of one or more extracts of *Polygonum cuspidatum* that are capable of killing cancer cells, carcinomas and tumors according to the present invention and an excipient.

The present invention further relates to a method of killing cancer cells, carcinomas and tumors, said method comprising contacting said cancer cells and tumors with a one or more extracts of *Polygonum cuspidatum* that are capable of acting as a photodynamic therapy agent according to the present invention in the presence of light and oxygen.

The present invention further relates to a method of killing cancer cells, carcinomas and tumors, said method comprising contacting said cancer cells and tumors with a one or more extracts of *Polygonum cuspidatum* that are capable of acting as a photodynamic therapy agent according to the present invention in the presence of light and oxygen wherein the said cancer cells, tumors, and carcinomas is selected from the group consisting of leukemia cells and tumors, melanoma cells and tumors, basal cell carcinoma, squamous cell carcinoma, verrucous carcinoma, minor salivary gland carcinomas, lymphomas, adenoid cystic cancer cells and tumors, bladder cells and tumors, breast cells and tumors, and colon cancer cells and tumors.

The present invention further relates to a method of killing cancer cells, carcinomas, and tumors, said method comprising contacting said cancer cells and tumors with a one or more extracts of *Polygonum cuspidatum* that are capable of acting as a photodynamic therapy agent according to the present invention and an excipient in the presence of light and oxygen.

The present invention further relates to a method of killing cancer cells, carcinomas, and tumors, said method comprising contacting said cancer cells and tumors with a one or more extracts of *Polygonum cuspidatum* that are capable of acting as a photodynamic therapy agent according to the present invention and an excipient in the presence of light and oxygen wherein the said cancer cells, tumors, and carcinomas are selected from the group consisting of leukemia cells and tumors, melanoma cells and tumors, basal cell carcinoma, squamous cell carcinoma, verrucous carcinoma, minor salivary gland carcinomas, lymphomas, adenoid cystic cancer cells and tumors, bladder cells and tumors, breast cells and tumors, and colon cancer cells and tumors.

The present invention further relates to compositions comprising an effective amount of one or more extracts of *Polygonum cuspidatum* that are useful as photodynamic therapy agents capable of treating benign oral cavity and oropharyngeal tumors.

The present invention further relates to a method of treating benign oral cavity and oropharyngeal tumors, said method comprising contacting said oral cavity and oropharyngeal tumors with a one or more extracts of *Polygonum cuspidatum* that are capable of acting as a photodynamic therapy agent according to the present invention in the presence of light and oxygen.

The present invention further relates to a method of treating benign oral cavity and oropharyngeal tumors said method comprising contacting said oral cavity and oropharyngeal tumors with a one or more extracts of *Polygonum cuspidatum* that are capable of acting as a photodynamic therapy agent according to the present invention in the presence of light and oxygen wherein the said benign oral cavity and oropharyngeal tumors are selected from the group consisting of eosinophilic granulomas, fibromas, granular cell tumors, karatoacanthomas, leiomyomas, osteochondromas, lipomas, schwannomas, neurofibromas, papillomas, condyloma acuminatums, verruciform xanthoma, pyogenic granulomas, rhabdomyoma, and odontogenic tumors.

The present invention further relates to a method of treating benign oral cavity and oropharyngeal tumors said method comprising contacting said oral cavity and oropharyngeal tumors with a one or more extracts of *Polygonum cuspidatum* that are capable of acting as a photodynamic therapy agent according to the present invention and an excipient in the presence of light and oxygen.

The present invention further relates to a method of treating benign oral cavity and oropharyngeal tumors said method comprising contacting said oral cavity and oropharyngeal tumors with a one or more extracts of *Polygonum cuspidatum* that are capable of acting as a photodynamic therapy agent according to the present invention and an excipient in the presence of light and oxygen wherein the said benign oral cavity and oropharyngeal tumors are selected from the group consisting of eosinophilic granulomas, fibromas, granular cell tumors, karatoacanthomas, leiomyomas, osteochondromas, lipomas, schwannomas, neurofibromas, papillomas, condyloma acuminatums, verruciform xanthoma, pyogenic granulomas, rhabdomyoma, and odontogenic tumors.

The present invention further relates to a process for preparing the extracts of *Polygonum cuspidatum* that are capable of photodynamic inactivation of microorganisms according to the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

Compositions of the Invention

More than 30 chemical compounds have been isolated from the root of *P. cuspidatum*. Among these constituents are: stilbenes, anthraquinones, flavonoids, phenols, sterols, essential oils, and amino acids. Components of *P. cuspidatum* root with reported biological activities that could be responsible for its use in traditional folk medicine include: resveratrol, polydatin, emodin, physcion, rhein, and anthraglycosides A and B. Some of these bioactives possess structural features that give rise to excited triplet states upon irradiation, which participate in photosensitization reactions. In some embodiments, the excited triplet states resulting upon irradiation participate in photosensitization reactions with oxygen and other species. Emodin, physcion, and their respective glycosylated derivatives, anthraglycosides A and B, produce photodynamic inactivation of microorganisms and photodynamic therapy effects. In some embodiments, isolation methods are developed to enrich the resulting extract in the photosensitizing molecules responsible for photodynamic therapy and photodynamic inactivation of microorganisms.

In one embodiment, the relative amount of various chemicals in the *P. cuspidatum* extract are as described in Table 1.

TABLE 1

Relative amounts of known *P. cuspidatum* components found in 1 mg of extract.

| Component | Amount per 1 mg extract (µg) |
|---|---|
| Polydatin | 63.2 |
| Resveratrol | 60.4 |
| Anthraglycoside B | 12.1 |
| Rhein | 5.6 |
| Emodin | 50.1 |
| Physcion | 10.4 |

Figure 6:
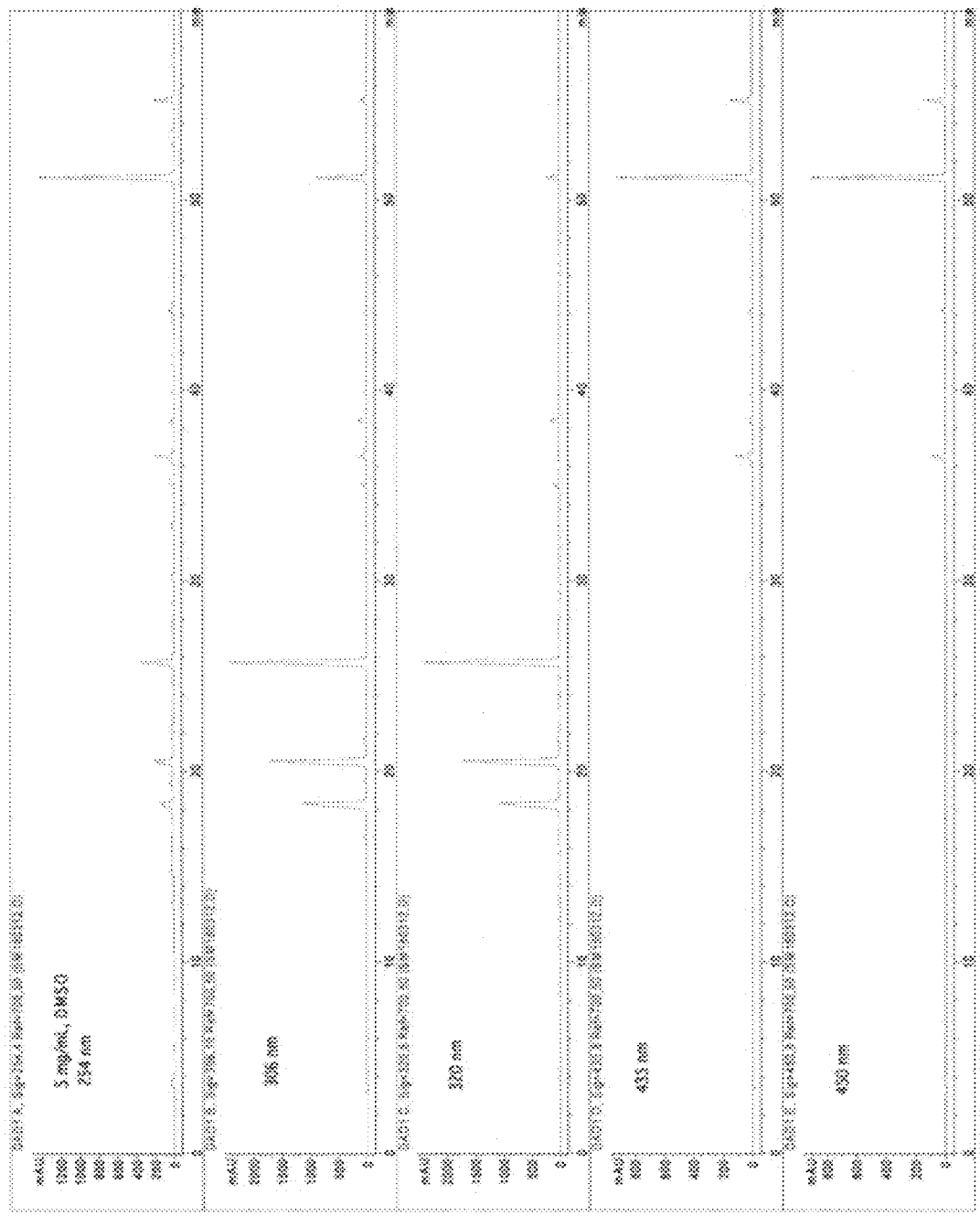
FIG. 6: HPLC trace of *Polygonum cuspidatum* extract.
Figure 15:
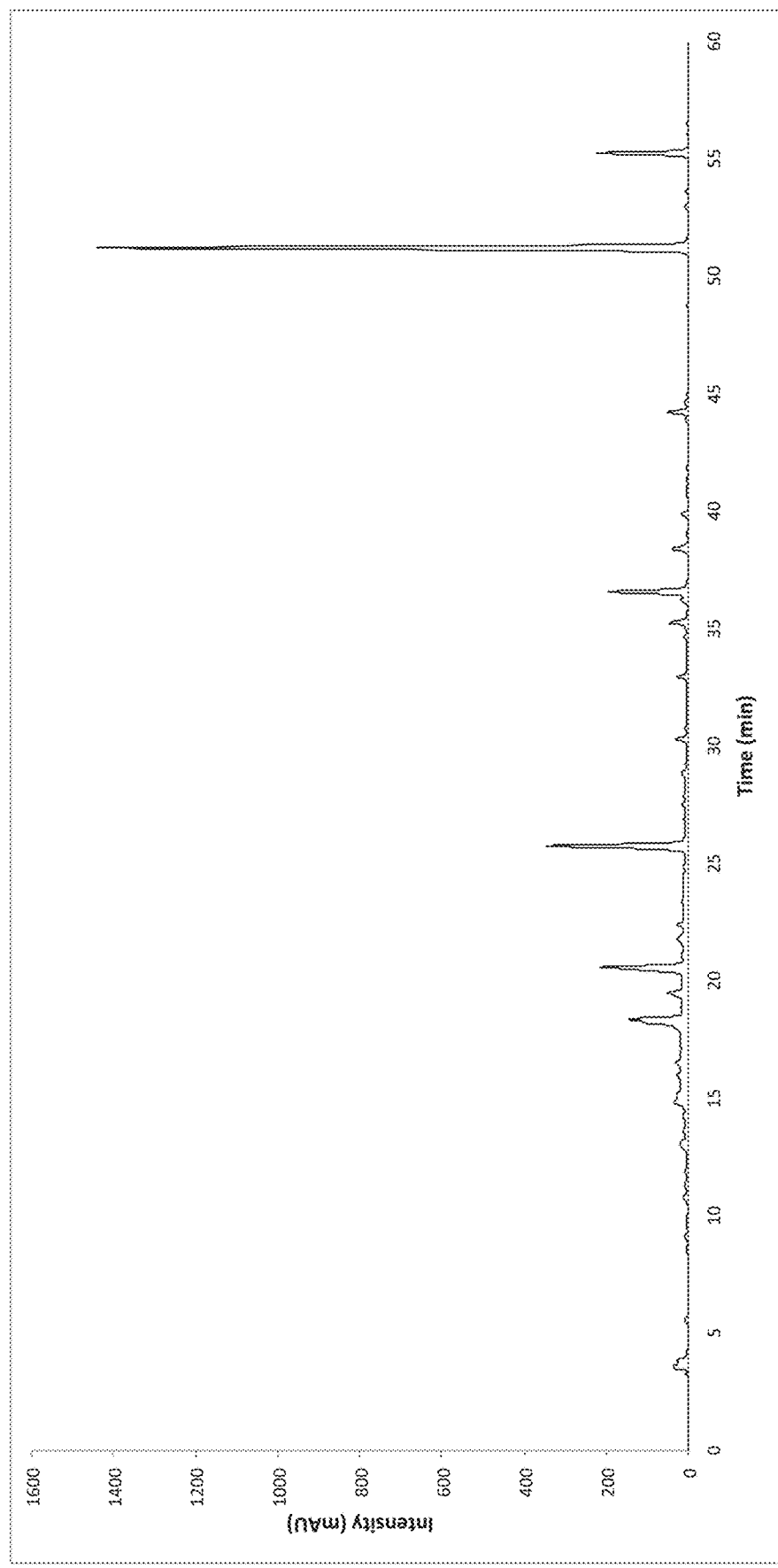
FIG. 15: HPLC chromatogram of *P. cuspidatum* extract.

Representative HPLC chromatograms of exemplary *P. cuspidatum* extracts are shown in FIGS. 6 and 15, and a list of retention times in Table 2. Five compounds have been identified as parts of the extract.

TABLE 2

HPLC retention times, intensities at 254 nm, and corresponding identities of known components.

| Time (min) | Intensity at 254 nm (AU) | Compound |
|---|---|---|
| 13.029 | 22.182 | Unknown |
| 14.882 | 36.22 | Unknown |
| 15.975 | 32.031 | Unknown |
| 16.509 | 33.62 | Unknown |
| 18.329 | 146.915 | Unknown |
| 19.455 | 50.72 | Unknown |
| 20.542 | 214.201 | Polydatin |
| 21.735 | 26.353 | Unknown |
| 25.709 | 349.624 | Resveratrol |
| 30.255 | 30.675 | Unknown |
| 32.902 | 26.428 | Unknown |
| 35.209 | 49.795 | Unknown |
| 36.169 | 20.306 | Unknown |
| 36.531 | 197.13 | Anthraglycoside B |
| 38.383 | 43.604 | Unknown |
| 44.189 | 52.799 | Rhein |
| 51.175 | 1440.695 | Emodin |
| 55.209 | 225.496 | Physcion |

It has been discovered that the antimicrobial properties of *P. cuspidatum* plant extract are significantly amplified by illumination with light. In one embodiment, illumination is with visible light. In another embodiment, illumination is with blue light. In another embodiment, illumination is with green light. In another embodiment, illumination is with ultraviolet (UV) light. In one embodiment, the light used has a wavelength between 200 nm and 400 nm. In one embodiment, the light used has a wavelength between 380 nm and 450 nm. In another embodiment, the light used has a wavelength between 400 nm and 700 nm. In another embodiment, the light used has a wavelength between 450 nm and 495 nm. In another embodiment, the light used has a wavelength between 495 nm and 570 nm. In another embodiment, the light used has a wavelength between 570 nm and 590 nm. In another embodiment, the light used has a wavelength between 590 nm and 620 nm. In another embodiment, the light used has a wavelength between 620 nm and 750 nm.

In some embodiments, the light irradiation is performed at a radiant exposure between 1 and 300 J $cm^{-2}$. In one embodiment, the radiant exposure of the light is about 28 J $cm^{-2}$. In another embodiment, the radiant exposure of the light is about 30 J $cm^{-2}$. In another embodiment, the radiant exposure of the light is about 35 J $cm^{-2}$. In another embodiment, the radiant exposure of the light is about 36 J $cm^{-2}$. In another embodiment, the radiant exposure of the light is about 50 J $cm^{-2}$. In another embodiment, the radiant exposure of the light is about 100 J $cm^{-2}$. In another embodiment, the radiant exposure of the light is about 150 J $cm^{-2}$. In another embodiment, the radiant exposure of the light is about 200 J $cm^{-2}$. In another embodiment, the radiant exposure of the light is about 250 J $cm^{-2}$. In another embodiment, the radiant exposure of the light is about 300 J $cm^{-2}$.

In some embodiments, the surface power density of the irradiating light is between 0.001 and 0.25 W $cm^{-2}$. In one embodiment, the surface power density of the irradiating light is about 0.001 W $cm^{-2}$. In one embodiment, the surface power density of the irradiating light is about 0.002 W $cm^{-2}$. In one embodiment, the surface power density of the irradiating light is about 0.003 W $cm^{-2}$. In one embodiment, the surface power density of the irradiating light is about 0.004 W $cm^{-2}$. In one embodiment, the surface power density of the irradiating light is about 0.005 W $cm^{-2}$. In one embodiment, the surface power density of the irradiating light is about 0.006 W cm$^{-2}$. In one embodiment, the surface power density of the irradiating light is about 0.007 W cm$^{-2}$. In one embodiment, the surface power density of the irradiating light is about 0.008 W cm$^{-2}$. In one embodiment, the surface power density of the irradiating light is about 0.009 W cm$^{-2}$. In one embodiment, the surface power density of the irradiating light is about 0.0096 W cm$^{-2}$.

In one embodiment, the surface power density of the irradiating light is about 0.01 W cm$^{-2}$. In another embodiment, the surface power density of the irradiating light is about 0.02 W cm$^{-2}$. In another embodiment, the surface power density of the irradiating light is about 0.0278 W cm$^{-2}$. In another embodiment, the surface power density of the irradiating light is about 0.03 W cm$^{-2}$. In another embodiment, the surface power density of the irradiating light is about 0.04 W cm$^{-2}$. In another embodiment, the surface power density of the irradiating light is about 0.05 W cm$^{-2}$. In another embodiment, the surface power density of the irradiating light is about 0.06 W cm$^{-2}$. In another embodiment, the surface power density of the irradiating light is about 0.07 W cm$^{-2}$. In another embodiment, the surface power density of the irradiating light is about 0.08 W cm$^{-2}$. In another embodiment, the surface power density of the irradiating light is about 0.09 W cm$^{-2}$. In another embodiment, the surface power density of the irradiating light is about 0.10 W cm$^{-2}$. In another embodiment, the surface power density of the irradiating light is about 0.15 W cm$^{-2}$. In another embodiment, the surface power density of the irradiating light is about 0.20 W cm$^{-2}$. In another embodiment, the surface power density of the irradiating light is about 0.25 W cm$^{-2}$.

This photodynamic effect was first demonstrated using bacteria from soil (FIG. 1) and was subsequently quantified with standard bacterial species purchased from ATCC (American Type Culture Collection). In some embodiments, against oral bacteria, the potency of phototoxic *P. cuspidatum* extracts exceeds the traditional antibiotic activity from chlorhexidine. These photoactive extracts give remarkable photodynamic therapy (PDT) and photodynamic inactivation effects across various harvest sites throughout Nova Scotia and New Brunswick, seasons, and cultivation methods (indoor vs. outdoor).

Surprisingly, extracts containing these compounds in relatively small percentages by weight are far more active than the pure anthraquinones in isolation and as mixtures at similar concentrations. In some embodiments, the increased activity has been observed at percentages by weight of less than 10%. The extract as a vehicle increases the photoactivity of components of *P. cuspidatum* in a way that has not been observed previously. To date, there are no reports of the photodynamic activity of *P. cuspidatum* extract, nor of the increases in its photoactivity relative to isolated components that comprise the extract.

Formulations of the Invention

The present invention also relates to compositions or formulations which comprise the *P. cuspidatum* extract according to the present invention. In general, the compositions of the present invention comprise an effective amount of *P. cuspidatum* extract according to the present invention which is effective for providing photodynamic inactivation (PDI) of microorganisms such as bacteria, viruses, fungi; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

It should be appreciated that excipients may be used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to ensure delivery of the ingredients safely to the appropriate physiological location for treatment. It should also be appreciated that advantage can be taken of the fact the *P. cuspidatum* extract of the present invention has improved cellular potency, pharmacokinetic properties, as well as improved oral bioavailability.

The present teachings also provide pharmaceutical compositions that include *P. cuspidatum* extract described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Liquid carriers can be used in preparing solutions, suspensions, emulsions, syrups, elixirs, and for inhaled delivery. The *P. cuspidatum* extract of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of *P. cuspidatum* extract to about 500 mg/kg of compound, and can be given in a single dose or in two or more doses. Such doses can be administered in any manner useful in directing the *P. cuspidatum* extract to the location of a microorganism or cancer cell in a subject or on a surface, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, the *P. cuspidatum* extract of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

To increase the effectiveness of the *P. cuspidatum* extract of the present teachings, it can be desirable to combine the *P. cuspidatum* extract with other agents effective in the treatment of the target disease. For example, other active compounds (i.e., other active ingredients or agents) effective in treating the target disease can be administered with the *P. cuspidatum* extract of the present teachings. The other agents can be administered at the same time or at different times than the *P. cuspidatum* extract disclosed herein.

The *P. cuspidatum* extract of the present teachings can be useful for the treatment or inhibition of a pathological condition or disorder in a mammal, for example, a human subject. The present teachings accordingly provide methods of treating or inhibiting a pathological condition or disorder by providing to a mammal the *P. cuspidatum* extract of the present teachings or a pharmaceutical composition that includes the *P. cuspidatum* extract of the present teachings in combination or association with pharmaceutically acceptable carriers. The *P. cuspidatum* extract of the present teachings can be administered alone or in combination with other therapeutically effective compounds or therapies for the treatment or inhibition of the pathological condition or disorder.

Non-limiting examples of compositions and formulations of the present invention include a *P. cuspidatum* extract in any relative amount from 0 to 100%. In some embodiments, the relative amount is expressed as weight per volume, i.e., w/v. For example, a 1% concentration of extract is understood to be 10 mg of extract per 1 mL of composition or formulation, i.e., 1%=10 mg/mL.

In various embodiments, the relative percentage of *P. cuspidatum* extract is between 0.01% and 20%. In one embodiment, the relative percentage of *P. cuspidatum* extract is between 0.005% and 0.1%. In other embodiments, the relative percentage of *P. cuspidatum* extract is between 0.01% and 1%. In other embodiments, the relative percentage of *P. cuspidatum* extract is between 0.1% and 1%. In one embodiment, the relative percentage of *P. cuspidatum* extract is about 0.1%. In another embodiment, the relative percentage of *P. cuspidatum* extract is about 0.2%. In another embodiment, the relative percentage of *P. cuspidatum* extract is about 0.3%. In another embodiment, the relative percentage of *P. cuspidatum* extract is about 0.4%. In another embodiment, the relative percentage of *P. cuspidatum* extract is about 0.5%. In another embodiment, the relative percentage of *P. cuspidatum* extract is about 0.6%. In another embodiment, the relative percentage of *P. cuspidatum* extract is about 0.7%. In another embodiment, the relative percentage of *P. cuspidatum* extract is about 0.8%. In another embodiment, the relative percentage of *P. cuspidatum* extract is about 0.9%. In another embodiment, the relative percentage of *P. cuspidatum* extract is about 1%. In one embodiment, the relative percentage of *P. cuspidatum* extract is about 5%. In another embodiment, the relative percentage of *P. cuspidatum* extract is about 10%. In another embodiment, the relative percentage of *P. cuspidatum* extract is about 15%. In another embodiment, the relative percentage of *P. cuspidatum* extract is about 20%.

In various other embodiments, the relative percentage of *P. cuspidatum* extract is between 20% and 100%. In one embodiment, the relative percentage of *P. cuspidatum* extract is about 25%. In another embodiment, the relative percentage of *P. cuspidatum* extract is about 30%. In another embodiment, the relative percentage of *P. cuspidatum* extract is about 35%. In another embodiment, the relative percentage of *P. cuspidatum* extract is about 40%. In another embodiment, the relative percentage of *P. cuspidatum* extract is about 45%. In another embodiment, the relative percentage of *P. cuspidatum* extract is about 50%. In another embodiment, the relative percentage of *P. cuspidatum* extract is about 55%. In another embodiment, the relative percentage of *P. cuspidatum* extract is about 60%. In another embodiment, the relative percentage of *P. cuspidatum* extract is about 65%. In another embodiment, the relative percentage of *P. cuspidatum* extract is about 70%. In another embodiment, the relative percentage of *P. cuspidatum* extract is about 75%. In another embodiment, the relative percentage of *P. cuspidatum* extract is about 80%. In another embodiment, the relative percentage of *P. cuspidatum* extract is about 85%. In another embodiment, the relative percentage of *P. cuspidatum* extract is about 90%. In another embodiment, the relative percentage of *P. cuspidatum* extract is about 95%. In another embodiment, the relative percentage of *P. cuspidatum* extract is about 100%.

Non-limiting examples of compositions according to the present invention include from about 0.001 mg to about 1000 mg of one or more of the *P. cuspidatum* extract according to the present invention and one or more excipients; from about 0.01 mg to about 100 mg of one or more of the *P. cuspidatum* extract according to the present invention and one or more excipients; and from about 0.1 mg to about 10 mg of one or more of the *P. cuspidatum* extract according to the present invention; and one or more excipients.

In some embodiments, the *P. cuspidatum* extract of the present invention may be formulated as a paste comprised of *P. cuspidatum* extract of the present invention incorporated into the paste in 0.005% to 10% by weight and at least one excipient.

In some embodiments, the *P. cuspidatum* extract of the present invention may be formulated as a paste comprised of the material listed in Table 3. In these formulations, the *P. cuspidatum* extract of the present invention is incorporated into the paste at 0.01% to 10% by weight.

TABLE 3

Exemplary formulations for a paste formulation of the
*P. cuspidatum* extract of the present invention

| Ingredients | % composition |
| --- | --- |
| Extract | 0.01 to 10.00 |
| Silica | 10.0 to 40.0 |
| Sorbitol | 0.0 to 5.0 |
| Glycerin | 0.0 to 5.0 |
| Xylitol | 0.0 to 1.5 |
| Sodium coco sulfate | 0.0 to 2.5 |
| Flavor | 0.0 to 1.5 |
| Xanthan gum | 0.0 to 1.5 |
| Carrageenan | 0.0 to 1.5 |
| Water | balance to 100% |

In a preferred embodiment, the *P. cuspidatum* extract of the present invention may be formulated as a paste comprised of the material listed in Table 4. In these formulations, the *P. cuspidatum* extract of the present invention is incorporated into the paste at 0.01% to 10% by weight.

TABLE 4

Preferred exemplary formulation for a paste formulation of the *P. cuspidatum* extract of the present invention

| Ingredients | % composition |
| --- | --- |
| Extract | 0.01-10.00 |
| Silica | 25.00 |
| Sorbitol | 1.00 |
| Glycerin | 1.00 |
| Xylitol | 0.50 |
| Sodium coco sulfate | 1.00 |
| Flavor | 0.25 |
| Xanthan gum | 0.50 |
| Carageenan | 0.50 |
| Water | balance to 100% |

In some embodiments, the *P. cuspidatum* extract of the present invention may be formulated as a paste comprised of the material listed in Table 5. In these formulations, the *P. cuspidatum* extract of the present invention is incorporated into the paste at 0.01% to 10% by weight.

TABLE 5

Exemplary formulations for a paste formulation of the *P. cuspidatum* extract of the present invention

| Ingredients | % composition |
| --- | --- |
| Extract | 0.01 to 10% |
| Abrasives | 20 to 45% |
| Detergent | 1 to 2% |
| Binding agents | 0.5 to 4% |
| Humectants | 10 to 30% |
| Flavoring, sweetening and coloring agents | 1 to 5% |
| Preservatives | 0.05 to 0.50% |
| Water | balance to 100% |

Abrasives include, but are not limited to, dicalcium phosphate, sodium metaphosphate, calcium carbonate, silica, hydrated alumina, zirconium silicate calcium pyrophosphate, and mica.

Detergents include, but are not limited to, sodium lauryl sulphate, sodium N-lauroyl sarcinate, sodium coco sulfate, and decyl glucoside.

Binding agents include, but are not limited to, cellulose, sodium carboxymethyl cellulose, carrageenans, xanthan gums, alginates, Polyvinyl methyl ether/maleic acid (PVM/MA) copolymer, gum arabic, and magnesium aluminum silicate.

Humectants include, but are not limited to, glycerol, sorbitol, and propylene glycol.

Flavoring, sweetening and coloring agents include, but are not limited to, peppermint, spearmint, cinnamon, wintergreen, menthol xylitol, and sodium saccharin.

Preservatives include, but are not limited to, alcohols, benzoates, formaldehyde, dichlorinated phenols, sodium benzoate, methyl paraben, and ethyl paraben.

In some embodiments, the *P. cuspidatum* extract of the present invention may be formulated as a gel comprised of *P. cuspidatum* extract of the present invention is incorporated into the gel at 0.01% to 10% by weight and at least one excipient.

In some embodiments, the *P. cuspidatum* extract of the present invention may be formulated as a gel comprised of the material listed in Table 6. In these formulations, the *P. cuspidatum* extract of the present invention is incorporated into the paste at 0.01% to 10% by weight.

TABLE 6

Exemplary formulations for a gel formulation of the *P. cuspidatum* extract of the present invention

| Ingredients | % composition |
| --- | --- |
| Extract | 0.01 to 10.00 |
| Sorbitol | 5.0 to 40.0 |
| Glycerin | 1.0 to 20.0 |
| Xylitol | 0.0 to 2.5 |
| Sodium coco sulfate | 0.0 to 5.0 |
| Flavor | 0.0 to 1.5 |
| Xanthan gum | 0.0 to 2.5 |
| Carageenan | 0.0 to 2.5 |
| Water | balance to 100% |

In a preferred embodiment, the *P. cuspidatum* extract of the present invention may be formulated as a gel comprised of the material listed in Table 7. In these formulations, the *P. cuspidatum* extract of the present invention is incorporated into the gel at 0.01% to 10% by weight.

TABLE 7

Preferred exemplary formulation for a gel formulation of the *P. cuspidatum* extract of the present invention

| Ingredients | % composition |
| --- | --- |
| Extract | 0.01 to 10.00 |
| Sorbitol | 25.00 |
| Glycerin | 10.00 |
| Xylitol | 0.5 |
| Sodium coco sulfate | 1.0 |
| Flavor | 0.25 |
| Xanthan gum | 1.0 |
| Carageenan | 1.0 |
| Water | balance to 100% |

In some embodiments, the *P. cuspidatum* extract of the present invention may be formulated as a foam comprised of *P. cuspidatum* extract of the present invention is incorporated into the foam at 0.01% to 10% by weight and at least one excipient.

In some embodiments, the *P. cuspidatum* extract of the present invention may be formulated as a foam comprised of the material listed in Table 8. In these formulations, the *P. cuspidatum* extract of the present invention is incorporated into the foam at 0.01% to 10% by weight.

TABLE 8

Exemplary formulations for a foam formulation of the
P. cuspidatum extract of the present invention

| Ingredients | % composition |
| --- | --- |
| Extract | 0.01 to 10.00 |
| Glycerin | 2.0 to 15.0 |
| Sorbitol | 2.0 to 15.0 |
| Xylitol | 0.0 to 2.5 |
| Flavor | 0.0 to 1.5 |
| Sodium coco sulfate | 0.0 to 2.5 |
| Decyl glucoside | 0.25 to 2.5 |
| Water | balance to 100% |

In a preferred embodiment, the P. cuspidatum extract of the present invention may be formulated as a foam comprised of the material listed in Table 9. In these formulations, the P. cuspidatum extract of the present invention is incorporated into the foam at 0.01% to 10% by weight.

TABLE 9

Preferred exemplary formulation for a foam formulation of
the P. cuspidatum extract of the present invention

| Ingredients | % composition |
| --- | --- |
| Extract | 0.01 to 10.00 |
| Glycerin | 5.0 |
| Sorbitol | 5.0 |
| Xylitol | 0.5 |
| Flavor | 0.25 |
| Sodium coco sulfate | 1.0 |
| Decyl glucoside | 1.0 |
| Water | balance to 100% |

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Materials and Methods

Dimethylsulfoxide (DMSO, 99.7%) was purchased from Fisher Scientific. 5% aqueous propylene glycol (PG) was prepared as a vehicle for in vivo testing by diluting commercial propylene glycol (99.5%, Sigma-Aldrich) with sterile deionized water. Toluidine Blue O (TB) was purchased from Sigma-Aldrich and diluted with sterile deionized water. Listerine Zero (Johnson & Johnson) was purchased at a local grocery store, and Oro-Clense (Germiphene Corporation, DIN 02209055) was obtained from a dental clinic. Chlorhexidine Digluconate (CHX) was purchased (Sigma-Aldrich) and diluted with sterile water.

Preparation of P. cuspidatum Extracts

Excess soil and root hairs were removed from the P. cuspidatum plant roots, which were subsequently cut into small pieces using a reciprocating saw and pruning shears. The root pieces were washed to remove excess soil and either chipped with an Earthwise Chipper Shredder (Model No. GS70014) or pulverized to a powder using the Commercial Vita-Mixer Maxi-4000 (Vitamix Corporation, Model No. 479044). Processed roots were allowed to dry for at least one day before extraction.

HPLC analyses were carried out on an Agilent/Hewlett-Packard 1100 series instrumentation (ChemStation Rev. A. 10.02 software) using a Hypersil GOLD C18 reversed-phase column with an A-B gradient (90%→0% A; A=0.2% formic acid in $H_2O$, B=MeOH). Reported retention times are corrected to within ±0.1 min. Column temperature was recorded to be 35° C., flow rate was 1 mL/min using a 20 µL injection of a sample prepared at 5 mg/mL. Absorbance values using UV/Vis DAD were recorded at 254 nm, 306 nm, 320 nm, 435 nm, and 450 nm. The trace shown in FIG. 15 was recorded at 254 nm.

P. cuspidatum Extract Preparation 1:

P. cuspidatum plants were harvested from Halifax, NS, in April 2012, transplanted in promix soil (ASB Greenwood), and kept in a phytotron under ambient conditions until processing in February 2013. Root powder (0.5 g) was Soxhlet extracted with 200 mL of ethanol until the solvent ran colorless. The ethanol extract was concentrated under reduced pressure to yield 132 mg of crude extract.

One skilled in the art would know and understand that the ethanol used in P. cuspidatum extract preparation 1 could be replaced with a suitable organic solvent such as methanol, isopropanol, n-propanol, n-butanol, tetrahydrofuran, 1,4-dioxane, methylene chloride, dichloroethane, ethyl acetate, and the like.

P. cuspidatum Extract Preparation 2:

P. cuspidatum Roots were harvested from 43 plants growing in Wolfville, N S in May 2013. The roots were transplated to a phytotron, where 22 specimens were propagated in native soil, and 21 specimens were propagated in a Promix soil. Plant specimens were collected from the phytotron from January 2014 through May 2014, when all 43 roots had been harvested. This material was chipped and combined, and 1.5 kg was extracted with 7.5 L of ethanol at room temperature. At 11 weeks a 40-mL aliquot was removed and concentrated in vacuo to give 497 mg of crude extract.

One skilled in the art would know and understand that the ethanol used in P. cuspidatum extract preparation 1 could be replaced with a suitable organic solvent such as methanol, isopropanol, n-propanol, n-butanol, tetrahydrofuran, 1,4-dioxane, methylene chloride, dichloroethane, ethyl acetate, and the like.

In other embodiments, extracts from other plants containing the photoactive ingredients that constitute P. cuspidatum would also be capable of eliciting PDI and PDT effects. For example, a photoactive compound contained in P. cuspidatum extract, emodin, is also found in the following plant families and genera. In some embodiments, extracts from Actinidiaceae (Actinidia), Amaranthaceae (Achyranthes), Asteraceae (Artemisia, Lactuca, Petasites), Bignoniaceae (Catalpa), Clusiaceae (Hypericum), Clusiaceae (Ploiarium), Clusiaceae (Psorospermum), Cupressaceae (Juniperus), Fabaceae (Cassia), Fabaceae (Phaseolus), Fabaceae (Pisum), Liliaceae (Aloe), Myrsinaceae (Myrsine), Plantaginaceae (Plantago), Poaceae (Agropyron), Polygonaceae (Rheum), Polygonaceae (Rumex), Rhamnaceae (Rhamnus), Rhamnaceae (Ventilago), Rosaceae (Fragaria), Rosaceae (Prunus), Saxifragaceae (Bergenia), Simaroubaceae (Bruceae), Simaroubaceae (Picramnia), and Vitaceae (Vitis) would serve the same purpose and be isolated in the same manner as the P. cuspidatum of the disclosure.

Bacterial Culture Preparation

Tryptic Soy Agar (TSA) was used for in vitro agar well diffusion tests. The media was prepared in a 500-mL Erlenmeyer flask by combining 7.5 g of Tryptic Soy Broth (TSB) with 3.75 g agar in 250 mL of deionized (DI) water. With cotton bung and foil covering the flask tops, the suspension was autoclaved at 121° C. for 1 hour. Well-mixed aliquots (20 mL) of liquid agar were transferred to 100×15 mm Petri dishes near a Bunsen burner with a sterile serological pipet (25 mL), and allowed to solidify. The average agar depth was 4 mm. The plates were labeled, sealed with Parafilm, and stored at 4° C. for one to two days before using.

Tryptic soy yeast-extract bacitracin agar (TSY20B), a selective medium for S. mutans recovery, was used for evaluating clinical samples (in vivo mouse oral PDI) (Schaeken, M. J. J Dent Res 1986, 65, 906-908.) The media was prepared in a 500 mL Erlenmeyer flask by combining 6.75 g TSB, 4.5 g agar, 2.5 g yeast extract, and 50 g sucrose in 250 mL distilled water, heating to boiling in microwave, covering the flask tops with cotton bung and foil, then autoclaving at 121° C. for 1 h. After slight cooling of the molten agar, 11.2 µL bacitracin (50 mg mL$^{-1}$) was incorporated and the hot agar was poured into 100×15 mm Petri dishes. The agar plates were labeled and sealed with Parafilm and stored at 4° C. for one to two days before use.

Bacterial Preparations

Using aseptic technique, a vial of Streptococcus mutans (S. mutans Clarke, ATCC 25175, designation NCTC 10449) was propagated by transferring half of the freeze-dried pellet, using a sterile loop, to a culture tube containing 2 mL Brain Heart Infusion medium (BHI, Oxoid), and gently mixed by swirling. The tube was capped loosely and placed in a 37° C. incubator for 24 hours. The following day, 10 serial dilutions were made ($10^{-1}$ to $10^{-8}$), then 0.1 mL aliquots from each dilution were spread on to fresh BHI agar plates (3.8% BHI) using sterile loops, allowed to dry with lids askew, then placed upside down in 37° C. incubator overnight. Purity of the colony growth was verified and the bacterial culture tube was subcultured by centrifuging (5000 rpm, 5 min), carefully pouring off the supernatant to waste, and replacing with 5 mL fresh media. Frozen stocks of S. mutans were prepared by transferring 500 µL aliquots of S. mutans culture to sterile 1.5 mL microcentrifuge tubes containing 500 µL sterile 70% glycerol in water. The tubes were mixed by vortexing briefly and subsequently stored in at −80° C.

Primary growth colony plates were prepared by transferring 50 µL frozen S. mutans to a sterile microcentrifuge tube containing 500 µL tryptic soy broth (TSB, Fluka 22092), and the solution was mixed well by vortexing. An aliquot of 50 µL was applied, using a quadrant streak method, to a TSA plate (3% TSB in agar), allowed to dry with the lid askew, and incubated overnight. The following morning the purities of the primary growth cultures were verified, then 1-2 colonies were transferred to a sterile microfuge tube containing 500 µL TSB and mixed well by pipetting up and down and vortexing. A secondary growth colony plate was prepared by transferring 50 uL of this mixture to a warmed TSA plate, quadrant streaked, allowed to dry as before, and stored at 37° C. The next morning the purities of the secondary growth cultures were again verified and subsequently used for agar well diffusion assays. These experiments used S. mutans colonies from secondary growth plates that were typically less than one week old. Secondary growth plates were replaced every 7-12 days.

In order to standardize the starting bacterial concentration for all experiments, a standard curve of McFarland barium sulfate turbidity standards, representing approximate bacterial concentrations, was constructed. McFarland barium sulfate standards 0.5, 1, 2, 3, 4, and 5, were prepared by following a published protocol (Isenberg H. Clinical Microbiology Procedures Handbook 2007 update, 2nd edition, American Society Microbiology, 2004). These standards represent approximately 1.5, 3, 6, 9, 12, 15×10$^8$ bacteria mL$^{-1}$, respectively. The absorbance values of the six barium sulfate standards at 625 nm, in a 1 cm path-length quartz cuvette, were recorded (Biochrom Libra S12 UV/Vis spectrophotometer, Biochrom Ltd.), a standard curve was made and the points were fit to a straight line. The equation of the trend line was used to determine all experimental bacterial inoculums.

Agar Diffusion Test Methods

An inoculum of S. mutans was prepared by transferring colonies from a room temperature secondary growth plate to a sterile 15 mL conical tube containing 5 mL sterile distilled water, and the contents were mixed well by vortexing. The absorbance at 625 nm was read and the approximate concentration was calculated according to the McFarland barium sulfate standard curve. The concentration was then adjusted to match a McFarland standard 0.5 (approximately 1.5×10$^8$ CFU mL$^{-1}$). A 300 µL aliquot of the inoculum was spread evenly over each TSA plate with sterile cotton tipped applicators (MedPro, Code. 018-426) to allow uniform growth of a bacterial lawn. The plates were dried with lids askew for about 30 min., and samples were delivered into bored holes or onto paper disks.

Bored Hole Agar Diffusion (BHAD)

Bored hole wells (5.5 mm in diameter, 4 mm in depth) were made in the TSA inoculated plates with the end of a of a 5¾" sterile Pasteur pipet. Typically, 5 wells were bored, one in the center for a control, and four in a symmetrical square around the control well in the center. Wells received 20 µL of sample.

Paper Disk Agar Diffusion (PDAD)

Paper disks were made from Whatman filter paper 1 (GE Healthcare Life Sciences, Code. 1001 090) with a hole punch, giving disks 6 mm in diameter. Paper disks were sterilized with ethanol and then allowed to dry before use. Using sterile forceps, paper disks were gently placed on the inoculated TSA in a pattern analogous to that of BHAD. Once paper disks were arranged appropriately, 10 µL of sample was applied to each disk.

Agar Diffusion Test on Extract Used for In Vivo Study

Samples were delivered to TSA plates prepared in duplicate (dark and light plates), each with a 0.5 McFarland barium standard inoculum (1.5×10$^8$ CFU mL$^{-1}$), according to the BHAD or PDAD methods described previously. Samples included: 3 mg mL$^{-1}$ chlorhexidine, deionized water, 5% PG, 3 mg mL$^{-1}$ P. cuspidatum extract of the disclosure in 5% propylene glycol, and 11 mg mL$^{-1}$ P. cuspidatum extract of the disclosure in 5% propylene glycol. Plates with samples were allowed to incubate at room temperature for 30 minutes, followed by irradiation of the light plates with a transparency projector (Bell & Howell, Model No. 310 LA) at a distance of 16.2 cm from the base of the projector for 15 minutes, yielding a light dose of 100 J cm$^{-2}$. During this irradiation period, the dark plates were kept protected from light for an equivalent period of time. Subsequent to light or dark treatment, the plates were incubated at 37° C. overnight and analyzed the following morning.

Agar Diffusion Concentration-Based Test

A concentration based assay of P. cuspidatum extract of the disclosure was performed using 0.1, 1, 10, 100 mg mL$^{-1}$ of extract in DMSO. Controls of 5 mg/mL chlorhexidine and DMSO only were included. TSA plates were prepared in duplicate (dark and light plates) with a 1.0 McFarland Standard (3.0×10$^8$ CFU mL$^{-1}$) according to the BHAD and PDAD methods. Light plates were irradiated in a photoreactor (Luzchem Research Ltd., Model No. LZC-4V) with 16 cool white bulbs (Osram Sylvania Inc., Code. F8T5-CW) for one hour to yield a light dose of 35 J cm$^{-2}$. During this irradiation period, the dark plates were kept protected from light for an equivalent period of time. Subsequent to light or dark treatment, the plates were incubated at 37° C. overnight and analyzed the following morning.

Agar Diffusion Comparative Tests

Commercial Listerine, Oro-Clense, and 1% TB were subjected to the agar diffusion analysis described in the concentration-based assay study alongside 10 mg mL$^{-1}$ and 100 mg mL$^{-1}$ *P. cuspidatum* extract in DMSO. The total light dose delivered to the light plates was 36 J cm$^{-2}$.

Microbroth Dilution Method on Planktonic Cultures

Minimum inhibitory concentration (MIC) and bactericidal concentration (MBC) were determined on suspension cultures growing in 96-well microtiter plates according to the micro-well dilution method (Sahin, F. et. al. J Ethnopharmacol 2003, 87, 61-65. Methods for Antimicrobial Susceptibility Testing of Anaerobic Bacteria; Approved Standard, 6th Edition. Wayne, Pa.: National Committee for Clinical Laboratory Standards; 2004.). Inoculum suspensions were prepared from secondary growth plates by combining 100 µL of diluted suspension (final concentration in assay 5×10$^5$ CFU mL$^{-1}$) and 100 µL of diluted extract in up to 5% propylene glycol in water to yield final extract concentrations between 0.01 and 50 mg mL$^{-1}$ in the assay. Two microtiter plates were prepared identically in parallel, with one receiving a light treatment of 35 J cm$^{-2}$ over one hour with light bulbs in a photoreactor after a pre-incubation for 30 min at 37° C. Thereafter, both light-treated and dark plates were incubated for 16 h at 37° C., and then the CFU mL$^{-1}$ was quantified for each well according to the Miles and Misra drop count technique (Miles, A. A, et. al. J Hyg (Lond) 1938, 38, 732-749) using TSA agar plates.

Ex Vivo Human Tooth Studies

Biofilm formation inhibition on human teeth by *P. cuspidatum* extracts and light was assessed according to a protocol adapted from the literature (Cho, Y. S. et. al. Biotechnol Bioprocess Eng 2010, 15, 359-364). Briefly, human teeth were kept in BHI broth (in 24-well microtiter plates) inoculated with *S. mutans* for 4 days at 37° C. in a candle jar (5% CO$_2$). For 3 minutes 3 times per day on days 2-4, teeth were removed and placed either in saline (control) or in *P. cuspidatum* extract (5 mg mL$^{-1}$). Following this short incubation period, half of the samples were irradiated with 100 J cm$^{-2}$ of light, while the other half were kept in the dark, and then both light and dark samples were returned to the inoculated BHI broth solutions. On day 5, samples were prepared for imaging, and on day 6, the biofilm formation on the surface of the teeth was examined by scanning electron microscopy (SEM) (Somayaji, K. et. al. Iran Endod J 2010, 5, 53-58).

Sample preparation for SEM analysis began with gentle washing in 0.5 M potassium phosphate buffer (pH 7.2, 5° C.). The teeth were then fixed in 2% glutaraldehyde at 5° C. for 20 hours, washed with phosphate buffered saline (PBS) for 15 minutes, and post-fixed in 1% (w/v) osmium tetroxide at 5° C. for 12 hours. Samples were then washed with PBS and dehydrated with ascending grades of acetone (10 minutes soak per grade): 30, 60, 80, and 100%. After storing in 100% ethanol, samples were transferred to liquid CO$_2$ and dried further in a critical point dryer before mounting and coating with a layer of gold palladium using a Polaron SC7670 sputter coater (100 s, 18-20 uA). Teeth surfaces were examined at up to 3500× magnification for evidence of biofilm formation with a JOEL JSM-5900LV SEM.

Example 1: Antibiotic Activities of *P. cuspidatum* Extracts

Figure 7:
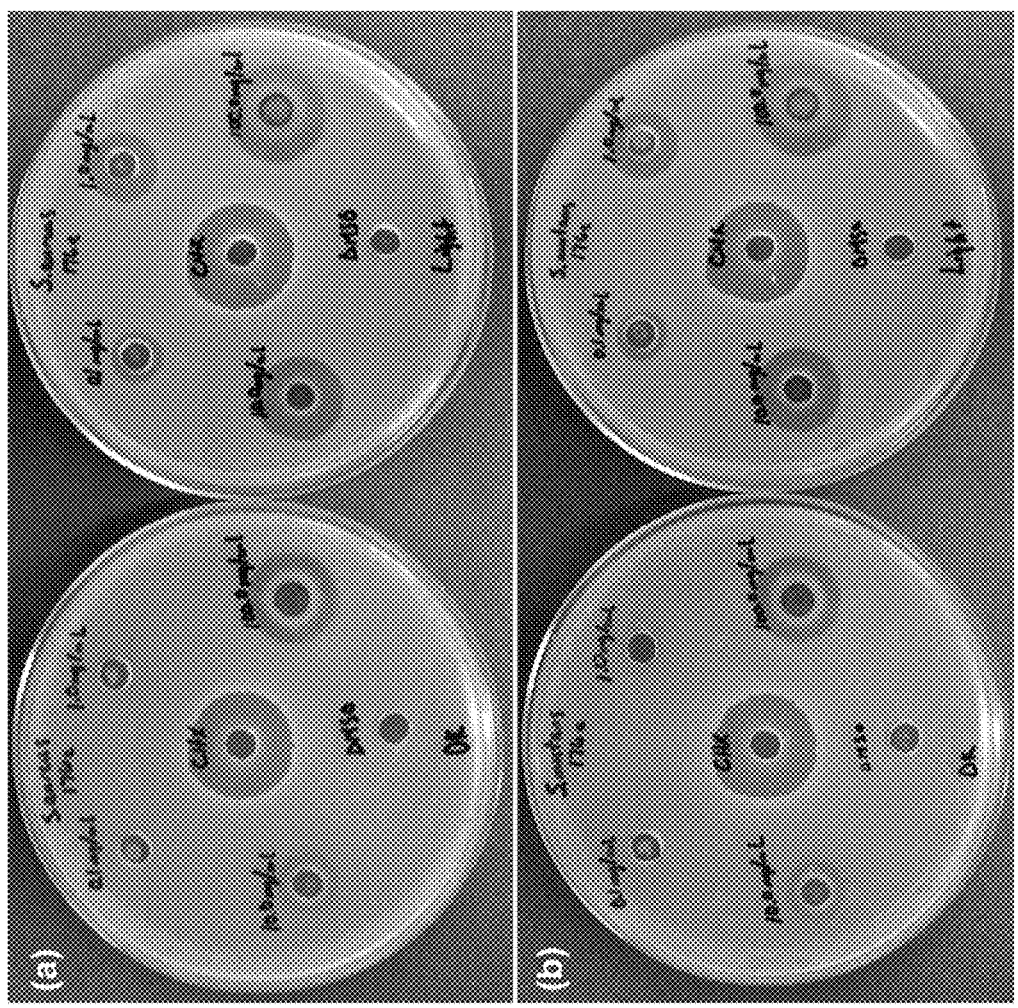
FIG. 7: Antimicrobial sensitivity of *S. aureus* (a) and *S. mutans* (b) to increasing concentrations of *P. cuspidatum* extract (0.1 mg mL$^{-1}$, 1.0 mg mL$^{-1}$, 10 mg mL$^{-1}$, and 100 mg mL$^{-1}$) delivered at 20 mL to TSA agar plates. Left: dark plate; right: plate irradiated with light (35 J cm$^{-2}$). Chlorhexidine and DMSO were included as positive and negative controls for antibiotic activity.
Figure 8:
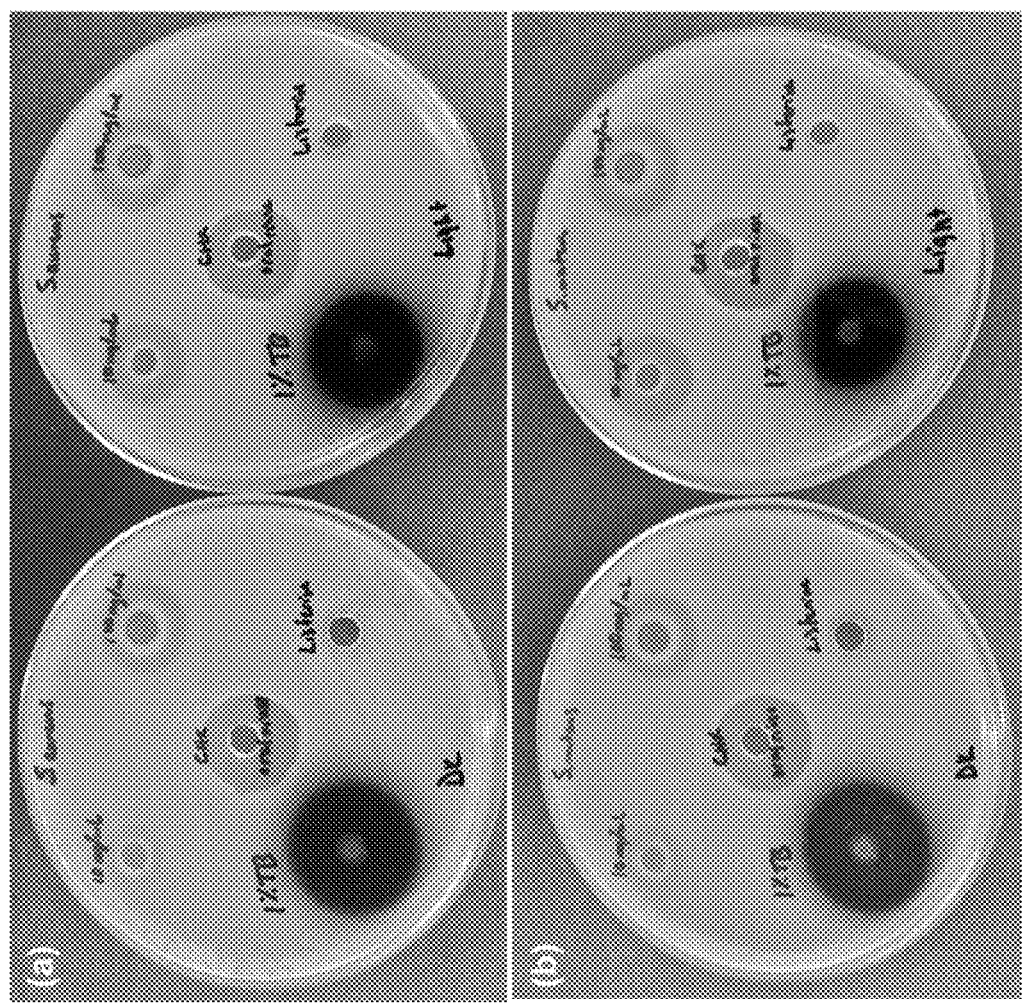
FIG. 8: Antimicrobial sensitivity of *S. aureus* (a) and *S. mutans* (b) to two concentrations of *P. cuspidatum* extract (10 mg mL$^{-1}$ and 100 mg mL$^{-1}$), commercial chlorhexidine (Oro-Clense), commercial Listerine Zero, and a 1% solution of Toluidine Blue (TB) probed by TSA agar diffusion. Left: dark plates; right: plates irradiated with light (36 J cm$^{-2}$).

Dark and light-mediated antibiotic activities of *P. cuspidatum* extracts were probed using a tryptic soy agar (TSA) diffusion test (Table 10; FIG. 7). Increasing concentrations of the extract in DMSO, from 0.01% to 10%, were tested against 300 µL of *S. aureus* or *S. mutans* inoculum (3×10$^8$ CFU mL$^{-1}$). After a 30 minute incubation period, one plate was irradiated with light for 1 hour to yield a total light dose of 35 J cm$^{-2}$, while the dark plate was protected from light. Inhibition zones were measured after a further 16 hour incubation period, and indicated the degree of bacterial sensitivity to these extract strengths and conditions. At the lowest concentrations, 0.01% and 0.1%, the *P. cuspidatum* extracts showed no discernible antibiotic activity against *S. aureus* or *S. mutans* in the dark. However, light activation of the *P. cuspidatum* extracts produced inhibition zones of 8 and 12 mm for the two concentrations, respectively, against both bacterial species tested. *P. cuspidatum* extract strengths of 1% gave dark inhibition zones of 9 mm against both bacteria, and 10% gave dark inhibition zones of 16 and 15 mm against *S. aureus* and *S. mutans*, respectively. Light activation of 1% and 10% *P. cuspidatum* extract solutions produced inhibition zones of 15 and 18 mm, respectively, against both types of bacteria. Notably, the inhibition zones produced by the highest concentration of *P. cuspidatum* extract were the same as those produced by the broad-spectrum antibiotic chlorhexidine at 40 times the commercial strength. When tested against the commercial chlorhexidine product Oro-Clense, photoactivated 1% *P. cuspidatum* extract was equally effective, and 10% *P. cuspidatum* extract was notably more active than chlorhexidine (Table 11; FIG. 8). By comparison, Listerine Zero had no antimicrobial effect in this assay. These results underscore the versatility of the light-responsive *P. cuspidatum* extract to act as a broad-spectrum antibiotic. Importantly, photodynamic inactivation of microorganisms acts immediately and indiscriminately, eliminating the threat of resistance that challenges traditional antibiotics.

TABLE 10

Antibiotic susceptibility inhibition zones measured in the agar diffusion test with increasing concentrations of *P. cuspidatum* extract; for reference these values (dark and light) for chlorhexidine were 18 mm against both bacteria.

| *P. cuspidatum* Extract | *S. mutans* (mm) | | *S. aureus* (mm) | |
| --- | --- | --- | --- | --- |
| (mg mL$^{-1}$) | Dark | Light | Dark | Light |
| 0.1 | 0 | 8 | 0 | 8 |
| 1.0 | 0 | 12 | 0 | 12 |
| 10 | 9 | 15 | 9 | 15 |

TABLE 11

Antibiotic susceptibility inhibition zones measured in the agar diffusion test for 1% (10 mg mL$^{-1}$) *P. cuspidatum* extract, 1% toluidine blue (TB), and two commercial products.

| | *S. mutans* (mm) | | *S. aureus* (mm) | |
| --- | --- | --- | --- | --- |
| Sample | Dark | Light | Dark | Light |
| *P. cuspidatum* Extract 1% | 10 | 16 | 9 | 15 |
| TB 1% | 15 | 15 | 15 | 16 |

TABLE 11-continued

Antibiotic susceptibility inhibition zones measured in the agar diffusion test for 1% (10 mg mL$^{-1}$) *P. cuspidatum* extract, 1% toluidine blue (TB), and two commercial products.

| Sample | S. mutans (mm) | | S. aureus (mm) | |
| --- | --- | --- | --- | --- |
|  | Dark | Light | Dark | Light |
| Listerine Zero | 0 | 0 | 0 | 0 |
| Oro-Clense | 15 | 15 | 14 | 14 |

Figure 3:
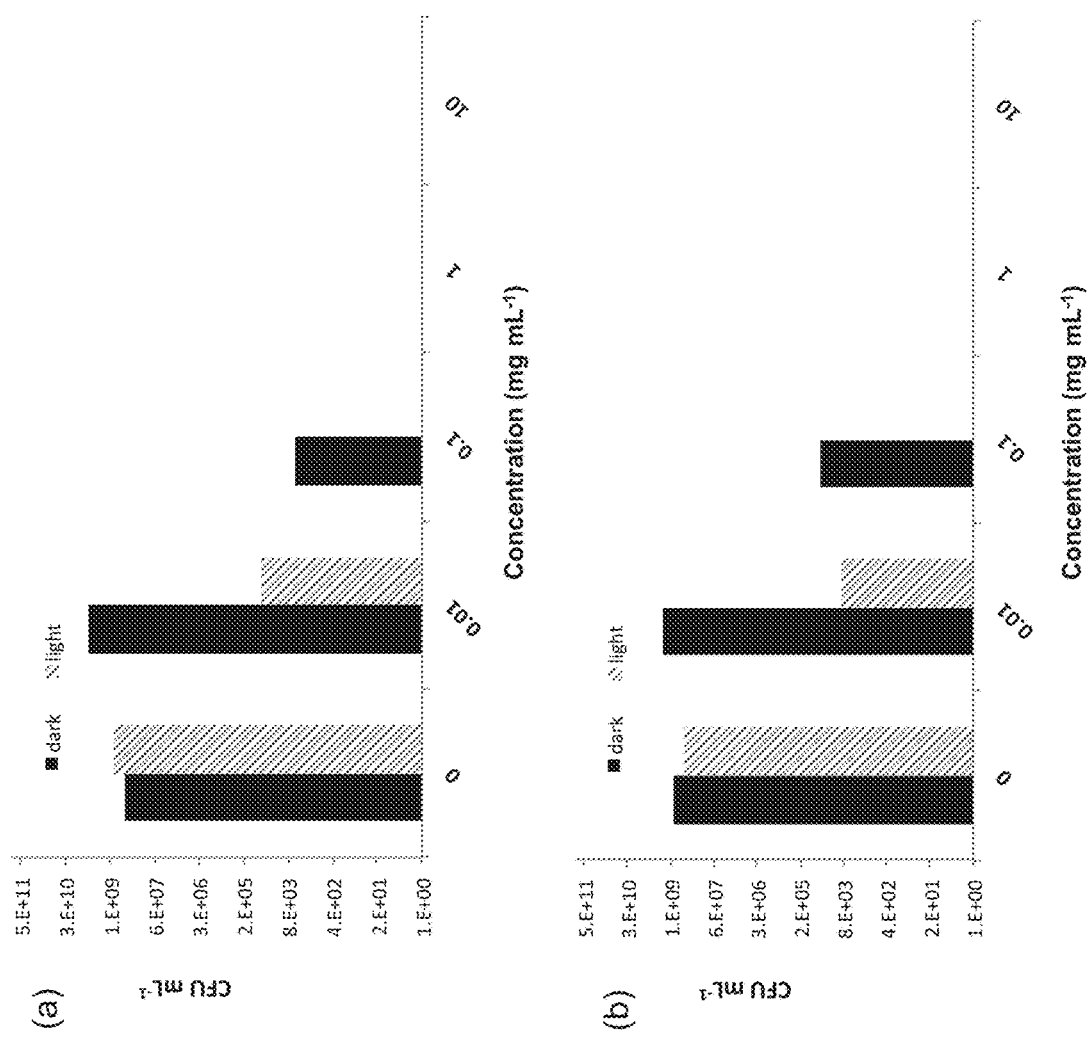
FIG. 3: Antibiotic activity of *P. cuspidatum* extract against (a) *S. aureus* and (b) *S. mutans* growing as planktonic cultures. Black bars represent samples kept in the dark; red bars are light-treated samples (35 J cm$^{-2}$). The absence of a bar indicates >99.9% bactericidal activity.

Extracts of *P. cuspidatum* were also effective in providing photodynamic inactivation of microorganisms against suspension cultures of *S. aureus* and *S. mutans* (FIGS. 3*a* and 3*b*, respectively). At 10 μg mL$^{-1}$, certain *P. cuspidatum* extracts gave no baseline antimicrobial activity toward *S. aureus*, while light activation produced over 5 log$_{10}$ of kill at the same concentration. At 100 μg mL$^{-1}$, the extracts behaved as traditional antibiotics, and light amplified the effect further, destroying more than 99.9% of all bacteria. This trend also held against *S. mutans*.

Figure 4:
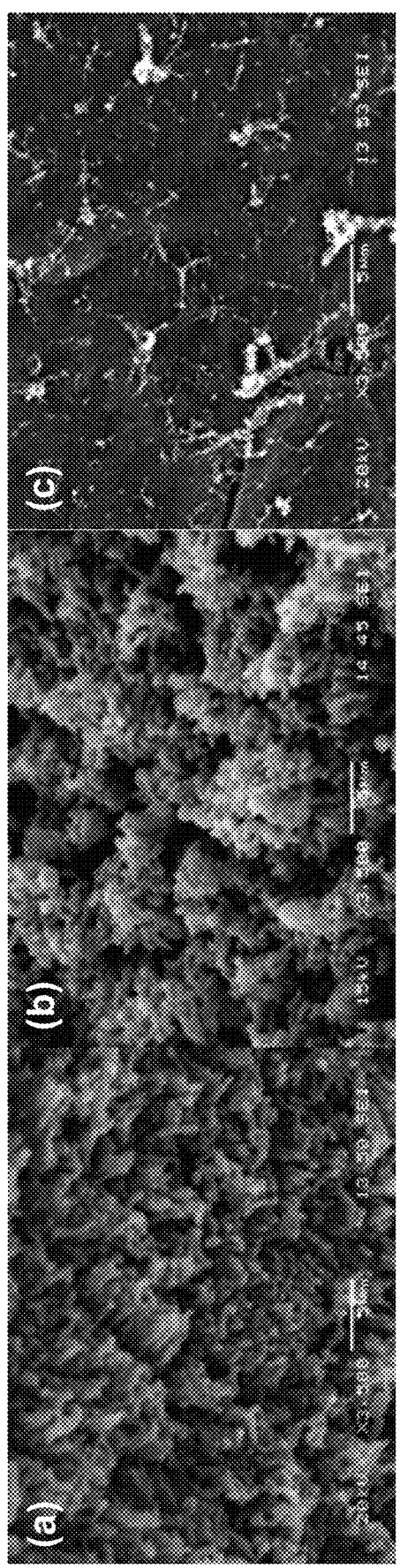
FIG. 4: Scanning electron micrographs (SEM) of human tooth crown: (a) microbiological biofilm on the untreated tooth surface (3500×), (b) morphological changes to the biofilm when treated with extract (3500×), and (c) inhibition of biofilm formation when treated with extract and irradiated with light (3500×).

*P. cuspidatum* extracts, when activated with light, inhibit the formation of *S. mutans* biofilm on the surfaces of human teeth (FIG. 4). A biofilm was allowed to form on individual teeth samples by maintaining the teeth in brain-heart infusion (BHI) broth inoculated with *S. mutans* over the course of four days. The resulting biofilm on an untreated tooth surface is shown in FIG. 4*a*. With *P. cuspidatum* extract treatment for three days (three times per day for three minutes), morphological changes to the biofilm were evident (FIG. 4*b*). However, when light (100 J cm$^{-2}$) was used to activate the *P. cuspidatum* extract following each three-minute treatment, no biofilm formed. As demonstrated in FIG. 4*c*, *P. cuspidatum* extracts act as potent photosensitizers for ex vivo photodynamic inactivation of microorganisms on human teeth.

Example 2: Antibiotic Activities of *P. cuspidatum* Extracts vs. Individual Components Notably, the photosensitizing power of *P. cuspidatum* extract gave rise to a photodynamic inactivation of microorganisms effect that was much greater than that of any one identifiable component of the extract. The anthraquinones, or their glycosylated derivatives, could be responsible for the photosensitizing effect of the extract. When isolated by fractionation, emodin produced the greatest photodynamic effect, followed by physcion. Their glycosides, anthraquinones B and A, respectively, were inactive. Commercial samples of anthraquinones produced photodynamic inactivation of microorganisms in the order emodin>physcion>rhein. In some *P. cuspidatum* extracts, the proportions of emodin and physcion are between 0.51-0.65% and 0.24-0.27% by weight, respectively. In an agar diffusion test of *P. cuspidatum* extract (40 μg) delivered to *S. mutans* (or *S. aureus*) coated TSA plates, photodynamic inactivation of microorganism inhibition zones were as large as 35-37 mm at their widest diameters and averaged 24-28 mm, and were not attenuated when the extracts were pre-exposed to a light treatment (FIG. 9; Table 12).

TABLE 12

Comparison of light-activated antimicrobial activity of *P. cuspidatum* extract to two of its constituent components (emodin and physcion) at their respective proportions found in the extract.

| Sample | S. mutans (mm) Light | S. aureus (mm) Light |
| --- | --- | --- |
| Extract | 26 (36) [a] | 26 (36) [a] |
| Emodin 0.001% [b] | 7.0 | 8.5 |
| Physcion 0.001% [b] | inactive | 8.5 |
| Combined standards at relative percentages [b, c] | 8.5 | 8.5 |

[a] Inhibition zone measured at largest distance;
[b] percent composition found in extract;
[c] standards used (emodin, physcion, rhein, polydatin, resveratrol, anthraglycoside B) mixed together at respective percent compositions found in extract.

By comparison, emodin and physcion standards tested at their corresponding weight percentages from some extracts, 0.20-0.26 μg for emodin and 0.10-0.11 μg for physcion, produced photodynamic inactivation of microorganism inhibition zones of 8-9 mm against *S. aureus*. Emodin gave a photodynamic inactivation of microorganism inhibition zone of 7 mm against *S. mutans*, while physcion was inactive. When emodin, physcion, and rhein standards were mixed in their relative proportions in the extract and tested in the same manner, the combined photodynamic inactivation of microorganism effect led to an inhibition zone of only about 8-9 mm. In this example, the *P. cuspidatum* extract was over four times more potent than the mixture of constituent components as commercial standards. Moreover, the photodynamic inactivation of microorganism effect of the mixed standards reflected that of the most active components together, suggesting that overall photodynamic inactivation of microorganism in the *P. cuspidatum* extract is not simply a linear combination of individual photosensitizer capacity.

Figure 14:
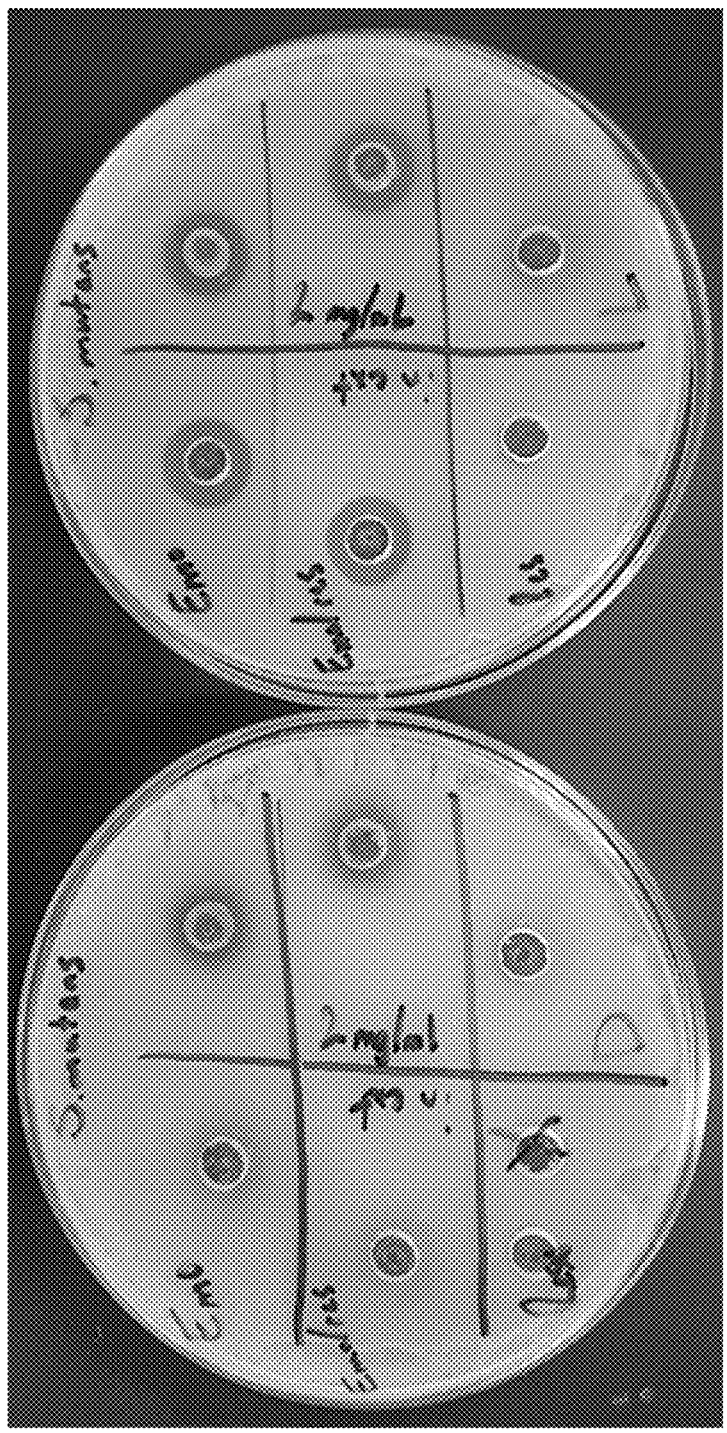
FIG. 14: Antimicrobial sensitivity of *S. mutans* to pure emodin or resveratrol and a mixture of emodin and resveratrol. Left: dark plates; right: plates irradiated with light (36 J cm$^{-2}$).

The stilbenoids, resveratrol and polydatin, do not amplify the photosensitizing power of the commercially tested anthraquinones. Resveratrol in combination with emodin did not alter the photoactivity of emodin. Inhibition zones measured for emodin (in the presence or absence of resveratrol) were 10 mm at concentrations as they occur naturally in some *P. cuspidatum* extracts (emodin 20 μL of 250 μg mL$^{-1}$=5 μg; resveratrol 20 μL of 300 μg mL$^{-1}$=6 μg) and at higher concentrations (20 μL of 2 mg mL$^{-1}$=40 μg). In addition resveratrol was inactive in the dark and with light activation under experimental conditions (FIG. 14).

Example 3: In Vivo Mouse Oral PDI

Figure 5:
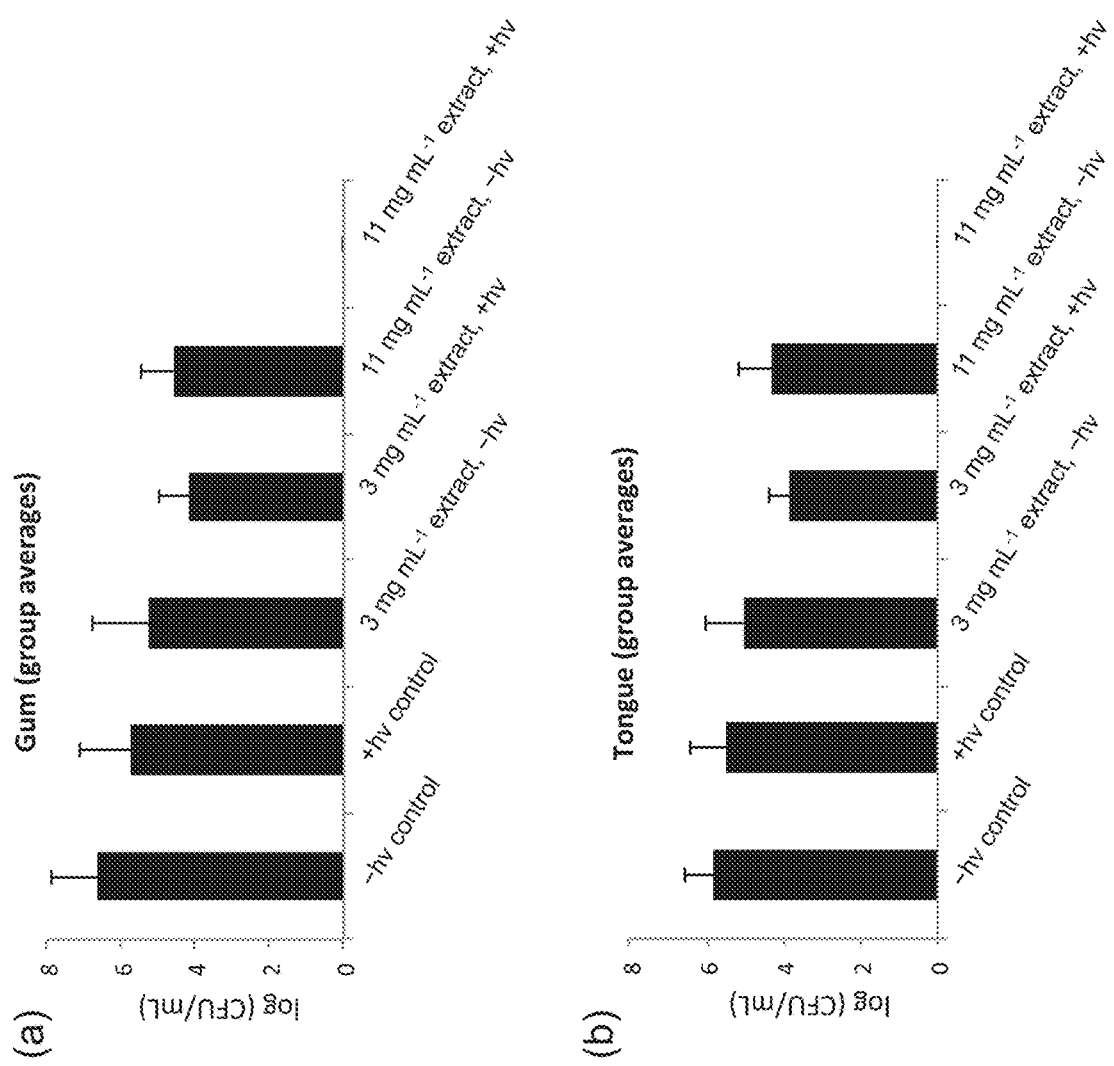
FIG. 5: Effect of *P. cuspidatum* extract-mediated photosensitization on the viability of *S. mutans* on (a) the upper gingival area surrounding the maxillary incisors (b) and the apex of the anterior dorsal region of the tongue of mice. The light dose was 30 J cm$^{-2}$ delivered over 5 min with LEDs. Control animals were treated with the vehicle used to formulate the extract (5% propylene glycol in water), and were either kept in the dark or given a light treatment. No bacteria were detected in animals treated with 11 mg mL$^{-1}$ extract and light.
Figure 10:
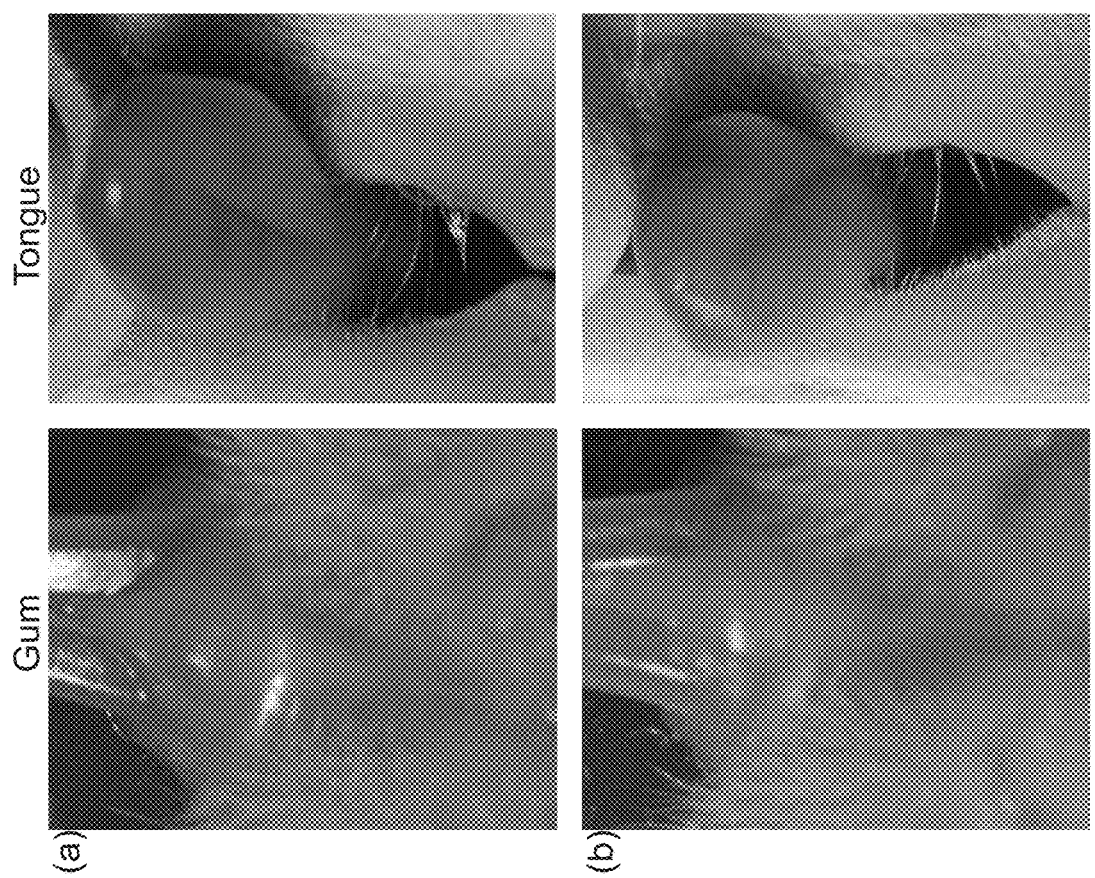
FIG. 10: Macroscopic views of the upper gingival area surrounding the maxillary incisors (left) and the apex of the anterior dorsal region of the tongue (right) of mice that received minimal intervention (a: vehicle 5% propylene glycol in water, dark) and maximum treatment (b: 11 mg mL$^{-1}$ extract, light). Photos were taken with a Pentax K20 camera equipped with a Vivitar Series 1 105 mm macro lens and AF540FGZ wireless flash.
Figure 11:
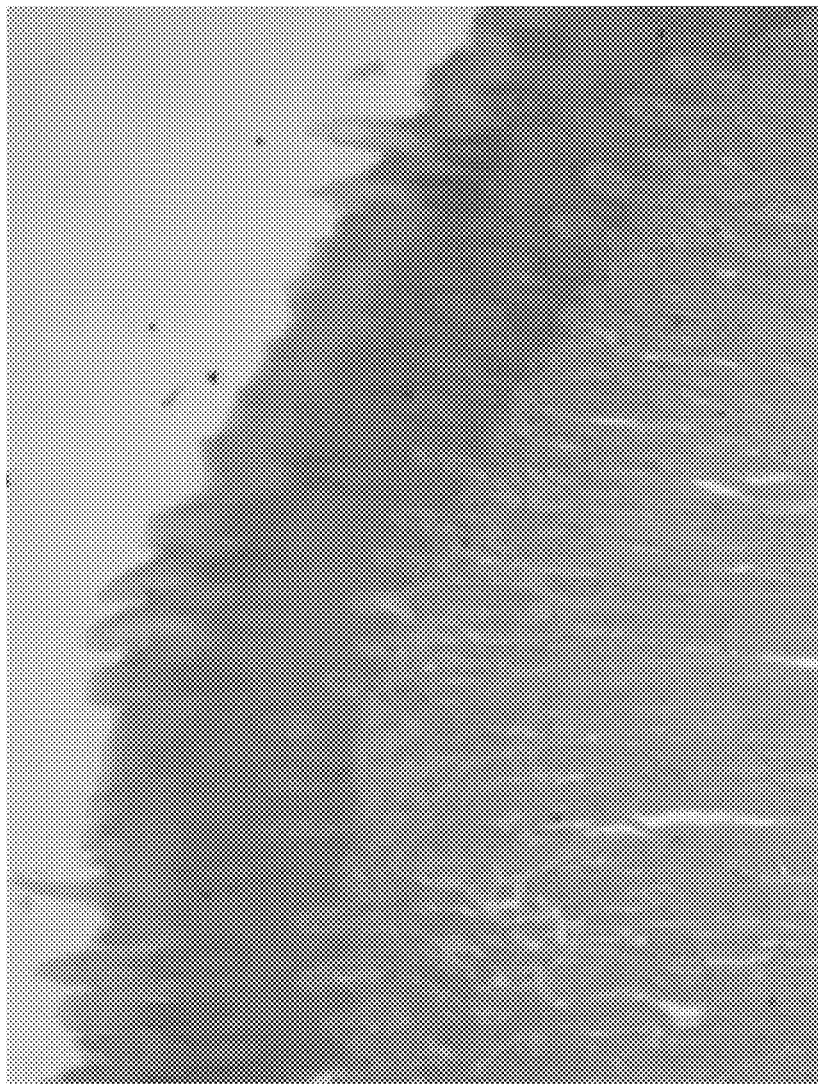
FIG. 11: Histological image (40× magnification) of a 6-μm slice of the anterior dorsal region of a mouse tongue that was treated with *P. cuspidatum* extract and light. Tissue shows no evidence of inflammatory infiltration due to the PDI treatment.

A male CD-1 mouse model was employed to determine whether photodynamic inactivation of microorganisms with *P. cuspidatum* extracts and light could effectively reduce bacterial load in the oral cavity. The effect of photosensitization with 30 J cm$^{-2}$ of light over 5 min on *S. mutans* viability was measured immediately following treatment (FIG. 5). The mice received one of the following treatments: (i) vehicle, dark; (ii) vehicle, light; (iii) 3 mg mL$^{-1}$ extract, dark; (iv) 3 mg mL$^{-1}$ extract, light; (v) 11 mg mL$^{-1}$ extract, dark; or (vi) 11 mg mL$^{-1}$ extract light. Groups (i) and (ii) were controls, and there was no significant difference between these two groups (p=0.16 for gums and 0.25 for tongues). There were reductions in bacterial viability upon *P. cuspidatum* extract treatment in the absence of light, but these reductions were only about 2 log$_{10}$ at the highest concentration of extract. When *P. cuspidatum* extract was used in conjunction with light, another 1-2 log$_{10}$ of kill was achieved at 3 mg mL$^{-1}$, while total destruction of all *S. mutans* occurred at 11 mg mL$^{-1}$ (p<0.001). The difference between dark and light treatment with 11 mg mL$^{-1}$ extract was approximately 5 $\log_{10}$ (p<0.001). These trends apply to both treatment areas. Importantly, there was no macroscopic evidence of ulceration or inflammation (FIG. 10). Upon histological evaluation, there was no evidence of inflammatory infiltration even with the highest concentration of *P. cuspidatum* extract and light (FIG. 11).

In Vivo Mouse Oral studies

Thirty male CD-1 mice approximately 10 weeks old and weighing 25-30 g (Charles River Laboratories International Ltd., St-Constant, Canada) were used in this study. Mice were housed in accordance with the regulations set by the Canadian Council of Animal Care. The mice were inoculated for one week prior to PDI treatment according to the following regimen. On day 1 they received 1% sucrose (Sigma-Aldrich) water in place of normal water. On days 2-7, they received a 1% sucrose water solution with a $1 \times 10^6$ CFU mL$^{-1}$ inoculum of *S. mutans*. Following treatment on day 8, all mice were placed into sterilized cages with fresh shavings and clean water. On the PDI treatment day, mice were further inoculated with 10 μL of water containing $2 \times 10^9$ CFU mL$^{-1}$ of *S. mutans* applied to the anterior dorsal region of the tongue and gingival region above the maxillary incisors. The aforementioned locations were the treatment regions for the study.

Two different concentrations of *P. cuspidatum* extract were used as photosensitizers in this study: 3 and 11 mg mL$^{-1}$ solutions in 5% propylene glycol in water as a vehicle. The irradiation source was a device fabricated in-house, consisting of 3 broad-spectrum, white light emitting diodes (LEDs) with a combined output of 0.1 W cm$^{-2}$. Lights were placed 2 cm from the oral opening of the mice during application, yielding a light dose of 30 J cm$^{-2}$ at this distance.

The 30 mice were randomly placed into one of six categories, with 5 mice per group: vehicle dark, vehicle light, 3 mg mL$^{-1}$ extract dark, 3 mg mL$^{-1}$ light, 11 mg mL$^{-1}$ dark, 11 mg mL$^{-1}$ light. Mice were treated one at time at random. They were anesthetized using a 0.1 mL IM (intramuscular) injection of ketamine and xylazine (mixture containing 50 mg kg$^{-1}$ of each). Once the specimen was fully anesthetized, it was situated on a special mount in a supine position. Access to the oral cavity was achieved using elastic bands to open the mouth (bands were placed around both sets of incisors) to expose the tongue and upper gingival area surrounding the maxillary incisors. First, 10 μL of water containing $2 \times 10^9$ CFU mL$^{-1}$ of *S. mutans* was delivered to the upper gingival area followed by 10 μL of sample (either vehicle, extract at 3 mg mL$^{-1}$ in vehicle, or extract at 11 mg mL$^{-1}$ in vehicle). The process was repeated on the anterior dorsal region of the tongue. These treatment areas were simultaneously irradiated with 30 J cm$^{-2}$ of LED light for 5 minutes or kept in the dark for 5 minutes. Bacterial swabs were taken from each treatment area using sterile endodontic paper points (Dia Dent, size 40). Two paper points were applied to each specified region for 60 seconds before being placed into screw-cap vials containing 0.5 mL of sterile Ringers-Peptone for further analysis. The specimens then were then released from the elastic bands and placed into clean cages to recover from anesthesia. Bacterial samples were processed within 3 hours.

Three days post-treatment, the specimens were anesthetized and swabbed for bacteria in a similar manner as on the treatment day, and then killed by cervical dislocation. The tongue and gums (including incisors of maxillary region) were immediately taken from the specimen and fixed in 0.5 mL of Bouin's Solution (Sigma-Aldrich) for histological analysis.

The number of bacterial colony forming units (CFU) was quantified using the Miles and Misra drop count technique (Miles, A. A. et. al. J Hyg (Lond) 1938, 38, 732-749). TSY20B (*S. mutans* specific agar) plates were marked into eight sectors corresponding to dilutions of $10^0$ to $10^{-7}$ of a sample to be analyzed. The undiluted 1× samples were serially diluted (7×10× serial dilutions) with sterile water. For each sample set dilution, a 20 μL drop of either the undiluted sample or the 10× diluted samples (8 total) was applied to each of the eight labeled sectors of the TSY20B plate, in order of increasing concentration ($10^{-7}$ to $10^0$). The plates were kept upright to dry before inversion and incubation at 37° C. for 18-24 h. Each sector was subsequently observed for growth. Sectors showing 2 to 50 colonies were counted, and Equation 1 was used to calculate average CFUs per mL of original sample.

$$CFU \ mL^{-1} = \frac{(\# \ of \ colonies)}{(volume) \times (dilution)} \quad \text{Equation 1}$$

Statistical analysis of the bacterial counts was performed using the Student's t-test. Differences between the individual treatment groups were considered significant at p values <0.05).

Histological Evaluation

Tongue and gum tissue specimens (including incisors of maxillary region) were refrigerated in fixative (Bouin's solution) at 4° C. for 2 days. The gum samples, including incisors, were prepped for decalcification by carefully removing the solution, replacing with fresh 0.5 mL Bouin's solution, and allowing vials to sit at room temperature for 24 hours. The solution was removed, and the samples were washed in slow running water (3×10 minutes). The samples were then carefully transferred to a sterile 24 well microplate containing 1 mL 10% EDTA in water (pH 7.36). The 10% EDTA solution was changed every 2 days for a period of 15 days, and the samples were placed in 70% ethanol for at least 24 hours. The tongue tissues, after 2 days in Bouin's solution, were washed once with 70% ethanol, and held in 70% ethanol for at least 24 hours. The samples were dehydrated to 100% ethanol, cleared in toluene and embedded in paraffin for histological evaluation with hematoxylin-eosin (H&E) stain.

Dehydration and Staining of Tissue Samples

Samples were dehydrated as follows: Tissue samples were suspended for 2 hours in 85% ethanol and then the solvent was removed. The tissue samples were then suspended for 1 hour in 95% ethanol and then the solvent was removed. The tissue samples were then suspended for 0.5 hour in 100% ethanol and then the solvent was removed. The tissue samples were then suspended in toluene for 1 hour, the solvent was removed, and the tissue samples were re-suspended in toluene. After 1 hour, the solvent was removed, and the tissue sample was suspended in hot liquid paraffin at 60° C. for 20 minutes under vacuum, and then the paraffin was removed. The paraffin suspension and removal was repeated two more times. Finally, samples were embedded in paraffin and left to harden at room temperature. The paraffin embedded tissues were mounted on wooden blocks and sectioned using a microtome (American Optical Company 820) at 6 μm thickness and transferred to labeled poly-L-lysine coated slides. For H&E staining, the paraffin was first dissolved away with 2 changes of xylene. Two changes of alcohol removed the xylene, and the slides were thoroughly rinsed with water to rehydrate the cells and tissue elements. The slides were dipped in hematoxylin stain, rinsed in tap water, and destained in 70% ethanol. An alcoholic solution of eosin was applied, and the slides were rinsed in several changes of alcohol to remove all traces of water. Two changes of xylene were used to clear the tissue, and then a polystyrene mountant (Permount®) was applied and covered with a glass cover slip. The slides were allowed to dry for at least 24 hours prior to microscopic analysis.

Example 4: Anti-Cancer Photo Dynamic Therapy

HL-60 Cell Culture

HL-60 human promyelocytic leukemia cells (ATCC CCL-240) were cultured at 37° C. under 5% $CO_2$ in RPMI 1640 (Mediatech Media MT-10-040-CV) supplemented with 20% FBS (PAA Laboratories, A15-701) and were passaged 3-4 times per week according to standard aseptic procedures. Cultures were started at 200,000 cells $mL^{-1}$ in 25 $cm^2$ tissue culture flasks and were subcultured when growth reached 800,000 cells $mL^{-1}$ to avoid senescence associated with prolonged high cell density. Complete media was prepared in 200 mL portions as needed by combining RPMI 1640 (160 mL) and FBS (40 mL, prealiquoted and heat inactivated), in a 250 mL Millipore vacuum stericup (0.22 μm) and filtering.

HL-60 Cell Viability Assays

Experiments were performed in triplicate in 96-well microtiter plates (Corning Costar, Acton, Mass.), where outer wells along the periphery contained 200 μL pH 7.4 phosphate buffered saline (PBS) with 2.68 mM potassium chloride, 1.47 mM potassium phosphate monobasic, 0.137 M sodium chloride, and 8.10 mM sodium phosphate dibasic to minimize evaporation from sample wells. HL-60 cells growing in log phase (approximately $8 \times 10^5$ cells) were transferred in 50 μL aliquots to inner wells containing warm culture medium (25 μL) and placed in a 37° C., 5% $CO_2$ water-jacketed incubator (Thermo Electron Corp., Forma Series II, Model 3110, HEPA Class 100) for 1 h to equilibrate. Ruthenium compounds were serially diluted with PBS and prewarmed before 25 μL aliquots of the appropriate dilutions were added to the cells and incubated at 37° C. under 5% $CO_2$ for drug-to-light intervals of 1 or 16 h. Untreated microplates were maintained in a dark incubator, while PDT-treated microplates were irradiated with light (400-700 nm, 27.8 mW $cm^{-2}$) using a 190 W BenQ MS510 overhead projector. The irradiation time was 1 h to yield light doses of approximately ~100 J $cm^{-2}$. Both dark and PDT-treated microplates were incubated for another 48 h at which point prewarmed, 10 μL aliquots of Alamar Blue reagent (Life Technologies DAL 1025) were added to all sample wells and allowed to incubate for 15-16 h at 37° C. under 5% $CO_2$ Cell viability was determined based on the ability of the Alamar Blue redox indicator to be metabolically converted to a fluorescent dye by live cells. Fluorescence was quantified with a Cytofluor 4000 fluorescence microplate reader with the excitation filter set at 530±25 nm and emission filter set at 620±40 nm. $EC_{50}$ values for cytotoxicity and photocytotoxicity were calculated from sigmoidal fits of the dose response curves using Graph Pad Prism 6.0 according to Equation 2, where $y_i$ and $y_f$ are the initial and final fluorescence signal intensities. For cells growing in log phase and of the same passage number, $EC_{50}$ values were reproducible to within ±25% in the submicromolar regime; ±10% below 10 μM; and ±5% above 10 μM.

$$y = y_i + \frac{y_i - y_f}{1 + 10^{(log\ EC_{50} - x) \times (Hill\ slope)}} \qquad \text{Equation 2}$$

A composition of the invention kills cancer cells via a non-specific, immediate mechanism of action mediated by photo-generated ROS and other reactive species ( ). One skilled in the art would recognize that the conditioned described for HL-60 cells could be adapted to other types of cancer cell lines. One skilled in the art would also know how to select the appropriate media and general techniques required to acquire assay data for other cancer cell lines.

Example 5: Antibiotic Activities of *P. cuspidatum* Extracts vs. Formulations Thereof Formulated extract is effective, with some formulations more effective than unformulated extract. As shown in).

Figure 9:
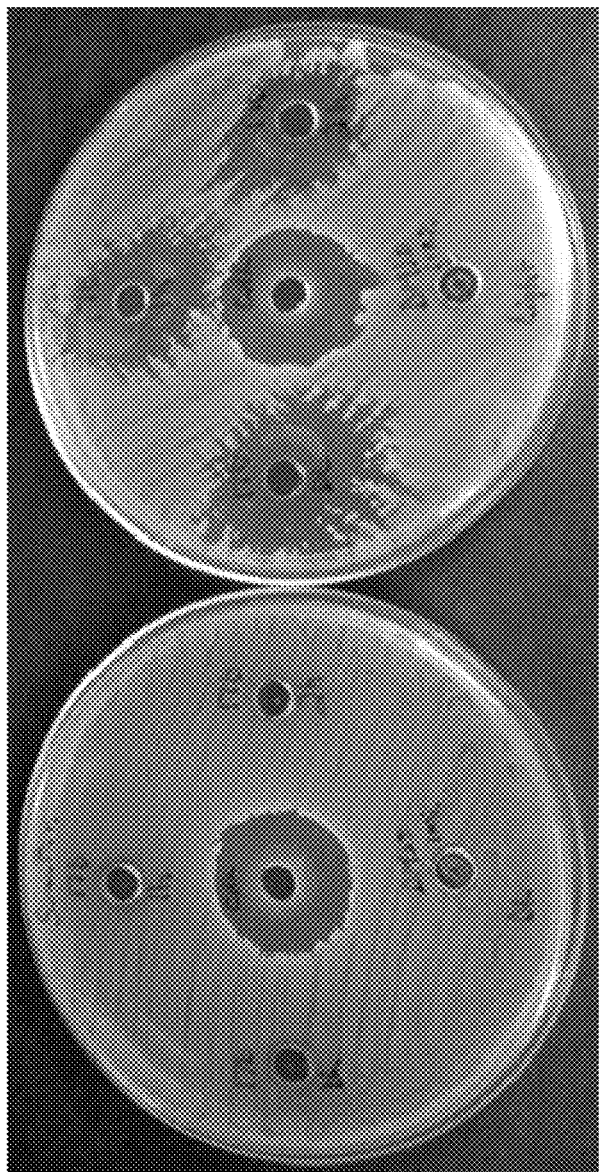
FIG. 9: Antimicrobial sensitivity of *S. mutans* to *P. cuspidatum* extract (40 mg, in DMSO as vehicle) and DMSO as a control. Left: dark plates; right: plates irradiated with light (36 J cm$^{-2}$). Labels on bored holes DK, 1 h, and 2 h correspond to *P. cuspidatum* extract that had no prior exposure to light, 1 h exposure, and 2 h exposure, respectively. *P. cuspidatum* extracts maintain their PDI activities after prolonged exposure to light, exhibiting photo-stability.

FIG. 9: 3, the formulated *P. cuspidatum* extract (Table 13), produces a larger inhibition zone (13.5 mm) in the agar diffusion assay compared to the unformulated *P. cuspidatum* extract (11 mm). Therefore, the light-triggered antibacterial activity of the extract can be amplified further with specialized formulation.

TABLE 13

Example of *P. cuspidatum* extract formulation

| Formula | FOAM | Date | Aug. 9, 2016 |
|---|---|---|---|
| Code | 10011959-F2 | | |
| Purpose | Sample Generation | | |
| Trial Outcome | This formula forms firm foam | | |

| | | | | Batch Size (g) 100 |
|---|---|---|---|---|
| Ingredients | Supplier | Supplier code | % | Weight |
| Water | L.V Lomas | GY006FGARCAT | 76.65 | 76.65 |
| Glycerin | ADM | 177010 | 10.00 | 10.00 |
| Sorbitol | Xylitol Canada | | 8.00 | 8.00 |
| Xylitol | David Michael & Co | 18111 | 1.00 | 1.00 |

TABLE 13-continued

| Example of P. cuspidatum extract formulation | | | | |
|---|---|---|---|---|
| Natural Flavor | Quadra | Eversoft ULS-30S | 0.35 | 0.35 |
| Sodium Lauroyl Glutamate | | | 3.00 | 3.00 |
| P. cuspidatum extract (bioactive) | | | 1.00 | 1.00 |
| Total Weight % | | | 100.00 | 100.00 |

Another exemplary embodiment of a P. cuspidatum formulation is described in Table 14.

TABLE 14

| Example of P. cuspidatum extract formulation | | | | | |
|---|---|---|---|---|---|
| Formula Code | | | FOAM 10011959-3 | | |
| Purpose | | | Sample Generation | | |
| Trial Outcome | | | | | |
| Ingredients | Supplier | Supplier Code | % | Weight (g) | Batch Size (g) 100 Weight (g) |
| Water | | | 79.55 | 397.75 | 79.55 |
| glycerin | L.V Lomas | GYC006FGARCAT | 10.00 | 50.00 | 10.00 |
| sorbitol | ADM | 177010 | 8.00 | 40.00 | 8.00 |
| xylitol | Xylitol Canada | | 1.00 | 5.00 | 1.00 |
| natural flavor | David Michael & Co | 18111 | 0.35 | 1.75 | 0.35 |
| sodium coco sulfate | Colonial Chemical | | 1.00 | 5.00 | 1.00 |
| bioactive | | | 0.10 | 0.50 | 0.10 |
| Total Weight % | | | 100.00 | 500.0 | 100.00 |

In other exemplary formulations the ranges of ingredients can be as described in Table 15.

TABLE 15

| Ranges of ingredients for exemplary foam formulation. | |
|---|---|
| Ingredient | Acceptable range (%) |
| Water | balance to 100% |
| Glycerin | 9.0-11.0 |
| Sorbitol | 7.0-9.0 |
| Xylitol | 0-2.0 |
| Natural Flavor | 0-1.0 |
| Sodium Lauroyl Glutamate | 2.7-3.3 |
| Bioactive | 0.1-1.5 |

Example 6: Toxicity of P. cuspidatum Extracts vs. Pure Emodin

Adherent CCD-1064SK normal skin fibroblasts (ATCC CRL-2076) were cultured in Iscove's Modified Dulbecco's Medium (IMDM) supplemented with 10% FBS (PAA Laboratories, A15-701), were incubated at 37° C. under 5% CO2, and were passaged 2~3 times per week according to standard aseptic procedures. CCD-1064SK cells were started at 200,000 cells mL$^{-1}$ in 75 cm$^2$ tissue culture flasks and were subcultured when growth reached 550,000 cells mL$^{-1}$ by removing old culture medium and rinsing the cell monolayer once with Dulbecco's phosphate buffered saline (DPBS 1×, Mediatech, 21-031-CV), followed by dissociation of the cell monolayer with trypsin-EDTA solution (0.25% w/v Trypsin/ 0.53 mM EDTA, ATCC 30-2101). Complete growth medium was added to the cell suspension to allow appropriate aliquots of cells to be transferred to new cell vessels. Complete growth medium was prepared in 250 mL portions as needed by combining IMDM (225 mL) and FBS (25 mL, prealiquoted and heat inactivated) in a 250 mL Millipore vacuum stericup (0.22 µm) and filtering.

Figure 12:
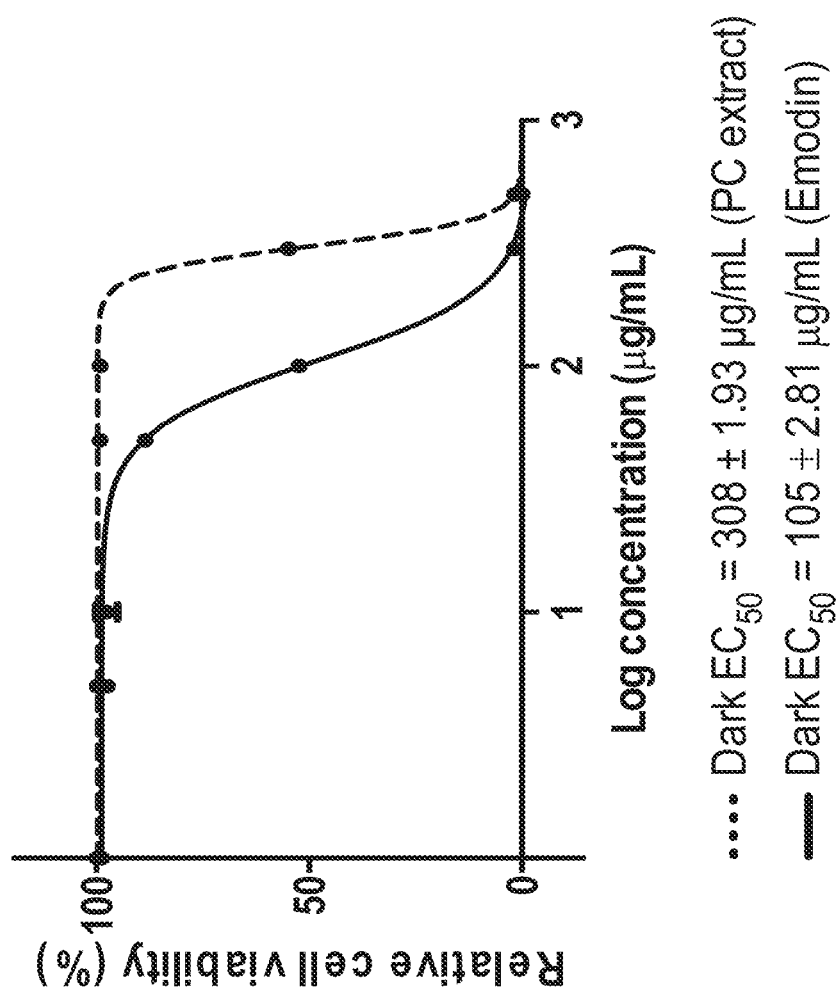
FIG. 12: Cytotoxicity of *P. cuspidatum* extract (dotted line) and emodin (solid line) toward skin fibroblast cells (CCD-1064Sk cell line).
Figure 13:
FIG. 13: Antimicrobial sensitivity of *S. mutans* to unformulated *P. cuspidatum* extract and formulated *P. cuspidatum* extract. Left: dark plates; right: plates irradiated with light (36 J cm$^{-2}$). Unformulated extract is a 1% solution of *P. cuspidatum* extract in DMSO. Formulated extract is a 1% solution of *P. cuspidatum* extract in the formulation shown in Table 13.

The P. cuspidatum extracts are 3-fold less toxic toward normal skin fibroblast cells relative to emodin in the dark (FIG. 12). This reduced dark toxicity is a significant advantage the extract holds over pure emodin as the photoactive antimicrobial.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of killing or inactivating microorganisms in the oral cavity of a subject, comprising:
    contacting the microorganisms in the oral cavity of a subject with a composition comprising an extract of Polygonum cuspidatum and an excipient; and
    irradiating the microorganisms with a source of light.

2. The method of claim 1, wherein the method is performed in the presence of oxygen.

3. The method of claim 1, wherein the microorganisms are part of a biofilm.

4. The method of claim 1, wherein the microorganisms are attached to a dental appliance.

5. The method of claim 4, wherein the dental appliance is selected from the group consisting of orthodontic brackets, bands, buttons, bonded attachments, bonded wire, crowns, inlays, onlays, restorations, dental abutments, and dental implants.

6. The method of claim 1, wherein the radiant exposure of the light is between 1 and 300 J cm', and the surface power density of the light is between 0.001 and 0.25 W $cm^{-2}$.

7. The method of claim 1, wherein the source of light is selected from the group consisting of a source of visible light, a source of blue light, and a source of green light.

8. The method of claim 1, wherein the excipient is selected from the group consisting of an abrasive, a detergent, a binding agent, a humectant, a flavoring agent, a sweetening agent, a coloring agent, a preservative, and water.

9. The method of claim 1, wherein the excipient is selected from the group consisting of water, silica, sorbitol, glycerin, xylitol, a coco sulfate salt, decyl glucoside, a flavoring agent, xanthan gum, carrageenan, and a glutamate.

10. The method of claim 1, wherein the composition is formulated as a formulation selected from the group consisting of a solution, a suspension, a paste, a gel, and a foam.

11. The method of claim 1, wherein the percentage of *Polygonum cuspidatum* extract in the composition is between 0.01 and 20%.

12. The method of claim 1, wherein the percentage of *Polygonum cuspidatum* extract in the composition is about 1%.

13. The method of claim 1, wherein the extract of *Polygonum cuspidatum* comprises at least one of emodin, physicion, rhein, and glycosylated derivatives thereof.

14. The method of claim 1, wherein the extract of of *Polygonum cuspidatum* comprises 0.51-0.65% emodin by weight.

15. The method of claim 1, wherein the light has a wavelength between 400 nm and 700 nm.

16. The method of claim 1, wherein the microorganisms are selected from the group consisting of bacteria, viruses, fungi, and protozoa.

17. The method of claim 1, wherein the microorganisms are on the surface of a tooth, in the a cavity in a tooth, on the surface of the gums, or on the mandibular or maxillary arches.

18. The method of claim 1, wherein the composition comprising an extract of *Polygonum cuspidatum* and an excipient comprises:
   between 0.1% and 10% *Polygonum cuspidatum* extract;
   between 20% and 45% abrasives;
   between 1% and 2% detergent;
   between 0.5% and 4% binding agents;
   between 10% and 30% humectants;
   between 1% and 5% flavoring, sweetening, and coloring agents; and
   between 0.05% and 0.5% preservatives.

19. A method of treating or preventing a microbial infection in the oral cavity of a subject, the method comprising the step of administering to the oral cavity a subject an effective amount of one or more extracts of *Polygonum cuspidatum* in the presence of light and oxygen.

* * * * *